(12) United States Patent
Hallahan

(10) Patent No.: US 7,049,140 B1
(45) Date of Patent: May 23, 2006

(54) X-RAY GUIDED DRUG DELIVERY

(75) Inventor: Dennis E. Hallahan, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/914,605

(22) PCT Filed: Apr. 28, 2000

(86) PCT No.: PCT/US00/11485

§ 371 (c)(1),
(2), (4) Date: Nov. 9, 2001

(87) PCT Pub. No.: WO00/66182

PCT Pub. Date: Nov. 9, 2000

Related U.S. Application Data

(63) Continuation-in-part of application No. 09/302,456, filed on Apr. 29, 1999.

(51) Int. Cl.
*C12N 5/08* (2006.01)

(52) U.S. Cl. .................. 435/372; 514/44; 424/450
(58) Field of Classification Search ........... 435/372; 514/44; 424/450
See application file for complete search history.

(56) References Cited

U.S. PATENT DOCUMENTS

| | | |
|---|---|---|
| 4,515,165 A | 5/1985 | Carroll |
| 4,619,823 A | 10/1986 | Yokoyama et al. .......... 424/1.1 |
| 4,670,386 A | 6/1987 | Sugaar |
| 5,093,104 A | 3/1992 | Kaminsky .................. 424/1.1 |
| 5,292,524 A | 3/1994 | Male et al. |
| 5,328,840 A | 7/1994 | Coller |
| 5,334,369 A | 8/1994 | Halushka et al. |
| 5,382,680 A | 1/1995 | Abraham et al. |
| 5,516,881 A | 5/1996 | Lee et al. |
| 5,693,627 A | 12/1997 | Schieven |
| 5,759,542 A | 6/1998 | Gurewich |
| 2003/0157025 A1* | 8/2003 | Unger et al. ............... 424/9.52 |

FOREIGN PATENT DOCUMENTS

| | | |
|---|---|---|
| DE | 2621311 | 11/1976 |
| EP | 229718 | 1/1987 |
| WO | WO8605693 | 10/1986 |
| WO | WO9306835 | 4/1993 |
| WO | WO 93/14791 | 8/1993 |
| WO | WO9320229 | 10/1993 |
| WO | WO9533496 | 12/1995 |
| WO | WO 96/12956 | 5/1996 |
| WO | WO9625947 | 8/1996 |

OTHER PUBLICATIONS

European Search Report for EP 00 93 5839.
Hirata et al., "Artificial Metastases and Decrease of Fibrinolysis in the Nude Mouse Lung After Hemithoracic Irradiation." Clin. Expl. Metastasis, vol. 2 (No. 4), p. 311-319, (1984).
Hirata, "Fate of Intravenously Injected Human Tumor Cells in the Lung of Nude Mice Following Whole-Body X-Irradiation," Invasion Metastasis, p. 61-70, (1985).
Stratton et al., "Imaging Arterial Thrombosis: Comparison of Technetium-99m-Labeled Monoclonal Antifibrin Antibodies and Indium-111-Platelets," J. Nucl. Med., p. 1731-1737, (1994).
Weichselbaum et al., "Gene Therapy Targeted by Radiation Preferentially Radiosensitizes Tumor Cells," Cancer Research, p. 4266-4269, (Aug. 15, 1994).
Song et al., "Combined Cytolytic Effect of X Irradiation and Cell-Mediated Immune Reactions on Tumor Cell in Vitro", *Radiology*, vol. 111; 213-214, Apr. 1974.
Bender et al., "Enhancement of Monoclonal Antibody Efficacy: The Effect of External Beam Radiation", *Hybridoma*, vol. 4 (No. 2); 129-134, Feb. 1995.

* cited by examiner

*Primary Examiner*—James Ketter
(74) *Attorney, Agent, or Firm*—Jenkins, Wilson, Taylor & Hunt, P.A.

(57) ABSTRACT

A method of delivering an active agent to a target tissue, particularly neoplastic tissue, vascular anomaly or tumor tissue, in a vertebrate subject. The method includes the steps of exposing the target tissue to ionizing radiation; and administering a delivery vehicle to the vertebrate subject before, after, during, or combinations thereof, exposing the target tissue to the ionizing radiation. The delivery vehicle includes the active agent and delivers the agent to the target tissue. Representative delivery vehicles include platelets; leukocytes; proteins or peptides which bind activated platelets; antibodies which bind activated platelets; microspheres coated with proteins or peptides which bind activated platelets; liposomes conjugated to proteins or peptides, platelets, or leukocytes which bind activated platelets, or antibodies which bind activated platelets; and combinations thereof.

47 Claims, No Drawings

X-RAY GUIDED DRUG DELIVERY

CROSS REFERENCE TO RELATED APPLICATIONS

This application is a continuation-in-part of co-pending U.S. patent application Ser. No. 09/302,456, filed Apr. 29, 1999, herein incorporated by reference in its entirety.

GRANT STATEMENT

This invention was made in part from government support under Grant Nos. CA70937 and CA58508 from the National Institute of Health. Thus, the U.S. Government has certain rights in the invention.

TECHNICAL FIELD

The present invention relates to a method and composition for selective in vivo delivery of therapeutic or imaging agents. More particularly, the present invention relates to a method and composition for selective in vivo delivery of therapeutic or imaging agents using ionizing radiation as a guide for the selective delivery.

Table of Abbreviations

| | |
|---|---|
| α - | alpha |
| AcNPV - | Autograph californica nuclear polyhidrosis virus |
| Ad - | Adenovirus or adenoviral |
| AVM - | arteriovenous malformation(s) |
| β - | beta |
| BPR - | bovine pancreatic ribonuclease |
| CAM - | cell adhesion molecule |
| CaMV - | Cauliflower mosaic virus |
| cGy - | centiGray |
| Gy - | Gray |
| CD62P - | P-selectin |
| CD63 - | cell adhesion molecule 63 |
| CT - | computed tomography |
| DDAVP - | depoprovera |
| DOPE - | dioleyol phosphatidyl ethanolamine |
| DT - | diphtheria toxin |
| ELISA - | enzyme linked immunosorbent assay |
| Fab - | antigen binding fragment of an immunoglobulin that has been digested by papain |
| F(ab')$_2$ - | antigen binding fragment of an immunoglobulin that has been digested by pepsin |
| Fc - | readily crystallized fragment of an immunoglobulin |
| γ - | gamma |
| GEL - | gelonin |
| GP-IIb - | platelet membrane glycoprotein IIb |
| GP-IIIa - | platelet membrane glycoprotein IIIa |
| GST - | glutathione S-transferase |
| h or hr - | hour(s) |
| HUVEC - | human umbilical vein endothelial cells |
| Ig - | immunoglobulin |
| IgG - | immunoglobulin G |
| IL-8 - | interleukin-8 |
| keV - | kiloelectron volts |
| kV - | kilovolt(s) |
| min - | minute(s) |
| MRI - | nuclear magnetic resonance imaging |
| MV - | megavolt(s) |
| nM - | nanomoles |
| PBS - | phosphate buffered saline |
| PPP - | platelet poor plasma |
| PRP - | platelet rich plasma |
| PAP - | pokeweed antiviral protein |
| PE - | *Pseudomonas* exotoxin |
| PET - | positron emission tomography |
| RES - | reticular endothelial system |
| RSVE - | reconstituted Sendai virus envelopes |
| SAP - | saporin |

Table of Abbreviations -continued

| | |
|---|---|
| SMPT - | 4-succinimidyloxycarbonyl-methyl-(2-pyridyldithio)-toluene |
| SPDP - | N-succinimidyl-3-(2-pyridyldithio)propionate |
| SPECT - | single photon emission computed tomography |
| TMV - | Tobacco mosaic virus |
| WPB - | Weibel-Palade body |

BACKGROUND ART

Ionizing radiation has been used to attenuate bleeding from tumors for the past three decades. See G. H. Fletcher, *Textbook of Radiotherapy*. Philadelphia, Lea and Febiger (1975). The primary examples of this use are in the treatment of menorrhagia from cervical carcinoma, hemoptysis from lung cancer and gastrointestinal bleeding from rectal and gastric carcinomas. The dose that is recommended to control bleeding from tumors is 400 to 500 cGy/fraction given for three consecutive days, as described by G. H. Fletcher, *Textbook of Radiotherapy*. Philadelphia, Lea and Febiger (1975) and by A. M. Markoe, Radiation Oncologic Emergencies, in *Principles and Practice of Radiation Oncology* 1267–1270 (1987). However, the efficacy of this regimen is not well documented. Moreover, the mechanism of radiation-induced control of bleeding is unknown.

Currently practiced methods of tumor specific drug delivery involve the use of antibody conjugates to liposomes and viral vectors. These methods are specific for tumor subtype or are nonspecific in localization. These limitations are significant in that, on the one hand, only certain types of tumors can be treated and, on the other hand, nonspecific localization produces undesirable collateral damage to otherwise healthy tissue.

Techniques for loading platelets have been disclosed in the art. For example, U.S. Pat. No. 5,292,524 issued to Male et al. on Mar. 8, 1994 discloses the preparation of loaded blood platelets which include a loading vehicle selected from the group consisting of liposomes and reconstituted Sendai virus envelopes. A diagnostic or therapeutic agent is encapsulated within the loading vehicle. However, there is no disclosure of a targeting technique for the loaded platelets.

U.S. Pat. No. 5,328,840 issued Jul. 12, 1994 to Coller discloses a method for preparing a targeted carrier erythrocyte by conjugating the erythrocyte with a particular polypeptide sequence. Thus, the targeting technique disclosed in Coller involves a complicated conjugation reaction.

In view of the shortcomings of the aforementioned techniques, there remains significant need in the field for advances in the tissue-selective delivery of therapeutic and imaging agents. Moreover, there remains a substantial need in the art for an improved method and composition for the selective delivery of therapeutic or imaging agents to neoplastic tissue. Indeed, a particularly desirable method and composition would provide for the specific delivery of a therapeutic or imaging agent to a wide variety of neoplasms while at the same time would maintain specificity for neoplastic tissue. Such a method and composition are currently not available in the art.

DISCLOSURE OF THE INVENTION

A method of targeting a tissue in a vertebrate subject for delivery of an active agent is disclosed. The method comprises the step of exposing the tissue to ionizing radiation before, after, during, or combinations thereof, administration of a delivery vehicle comprising the active agent to the vertebrate subject.

A method of delivering an active agent to a target tissue in a vertebrate subject is also disclosed. The method comprises the steps of exposing the target tissue to ionizing radiation; and administering a delivery vehicle to the vertebrate subject before, after, during, or combinations thereof, exposing the target tissue to the ionizing radiation, the delivery vehicle comprising the active agent, whereby the delivery vehicle aggregates in the target tissue to thereby deliver the agent to the target tissue.

Neoplasms and vascular anomalies comprise examples of target tissues. Therapeutic and imaging agents are particular active agents. Thus, a method of treating a neoplasm in a vertebrate subject is also disclosed herein.

A delivery vehicle for use in targeted delivery of an active agent is also provided in accordance with the present invention. The delivery vehicle comprises a targeting agent that preferentially binds a radiation inducible target in a target tissue. The delivery vehicle can further comprise a carrier, an active agent, or both a carrier and an active agent.

It is therefore an object of the present invention to provide an improved method and composition for selectively delivering an active agent to a target tissue, and particularly to neoplastic tissue or vascular anomaly, in a vertebrate subject. The object is achieved in whole or in part by the present invention.

An object of the invention having been stated hereinabove, other objects will become evident as the description proceeds, when taken in connection with the accompanying Examples as best described hereinbelow.

DETAILED DESCRIPTION OF THE INVENTION

Disclosed herein is the surprising observation that platelets aggregate in tumor vessels in a dose and time dependent manner when the tumor is irradiated with ionizing radiation, such as X-radiation. A method for delivering an active agent to a target tissue, such as tumor tissue or other neoplastic tissue, using a delivery vehicle comprising the active agent, and using ionizing radiation to target the tissue of interest is thus provided in accordance with the present invention.

Also disclosed herein is the surprising observation that expression of the cell adhesion molecule P-selectin is localized in the vascular lumen of tumor blood vessels when the tumor is irradiated. This observation was made in a wide variety of tumors. Although applicant does not wish to be bound by any particular theory of operation, it is contemplated that P-selectin mediates platelet aggregation in irradiated tumor blood vessels.

While the following terms are believed to be well understood by one of ordinary skill in the art, the following definitions are set forth to facilitate explanation of the invention.

The term "ionizing radiation" is meant to refer to any radiation where a nuclear particle has sufficient energy to remove an electron or other particle from an atom or molecule, thus producing an ion and a free electron or other particle. Examples of such ionizing radiation include, but are not limited to, gamma rays, X-rays, protons, electrons and alpha particles. Ionizing radiation is commonly used in medical radiotherapy and the specific techniques for such treatment will be apparent to a skilled practitioner in the art.

The term "delivery vehicle" as used herein is meant to refer to any cell, molecule, peptide, conjugate, construct, article or other vehicle as would be appreciated by one of ordinary skill in the art after reviewing the disclosure of the present application that can be used to carry an active agent to a target tissue in accordance with the present invention. A particular delivery vehicle is characterized by an ability to preferentially bind activated platelets. Thus, a delivery vehicle of the present invention can comprise a component selected from the group including but not limited to a platelet; a leukocyte; a proteins or peptide that binds a radiation inducible target; an antibody that binds a radiation inducible target; a microsphere coated with a protein or peptide that binds a radiation inducible target; a liposome conjugated to a protein or a peptide that binds a radiation inducible target; a liposome conjugated to an antibody that binds a radiation inducible target; a liposome conjugated to a platelet or a leukocyte; and combinations thereof. A provided microsphere can be coated with albumin, in that as disclosed in U.S. Pat. No. 5,969,936, albumin can be used to link targeting agents, e.g. targeting peptides, to the microsphere.

The term "active agent" is meant to refer to compounds that are therapeutic agents or imaging agents.

The term "therapeutic agent" is meant to refer to any agent having a therapeutic effect, including but not limited to chemotherapeutics, toxins, radiotherapeutics, or radiosensitizing agents.

The term "chemotherapeutic" is meant to refer to compounds that, when contacted with and/or incorporated into a cell, produce an effect on the cell, including causing the death of the cell, inhibiting cell division or inducing differentiation.

The term "toxin" is meant to refer to compounds that, when contacted with and/or incorporated into a cell, produce the death of the cell.

The term "radiotherapeutic" is meant to refer to radionuclides which when contacted with and/or incorporated into a cell, produce the death of the cell.

The term "radiosensitizing agent" is meant to refer to agents which increase the susceptibility of cells to the damaging effects of ionizing radiation or which become more toxic to a cell after exposure of the cell to ionizing radiation. A radiosensitizing agent permits lower doses of radiation to be administered and still provide a therapeutically effective dose.

The term "imaging agent" is meant to refer to compounds which can be detected.

The term "neoplasm" is meant to refer to an abnormal mass of tissue or cells. The growth of these tissues or cells exceeds and is uncoordinated with that of the normal tissues or cells and persists in the same excessive manner after cessation of the stimuli which evoked the change. These neoplastic tissues or cells show a lack of structural organization and coordination relative to normal tissues or cells which usually results in a mass of tissues or cells which can be either benign or malignant. Representative neoplasms thus include all forms of cancer, benign intracranial neoplasms, and aberrant blood vessels such as arteriovenous malformations (AVM), angiomas, macular degeneration, and other such vascular anomalies. As would be apparent to one of ordinary skill in the art, the term "tumor" typically refers to a larger neoplastic mass.

As used herein, neoplasm includes any neoplasm, including particularly all forms of cancer. This includes, but is not limited to, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, and the like. This also includes, but is not limited to, solid tumors, solid tumor metastases, angiofibromas, retrolental fibroplasia, hemangiomas, Karposi's sarcoma and the like cancers which require neovascularization to support tumor growth.

The phrase "treating a neoplasm" includes, but is not limited to, halting the growth of the neoplasm, killing the neoplasm, reducing the size of the neoplasm, or obliterating a neoplasm comprising a vascular anomaly. Halting the growth of the neoplasm refers to halting any increase in the size of the neoplasm or the neoplastic cells, or halting the division of the neoplasm or the neoplastic cells. Reducing the size of the neoplasm relates to reducing the size of the neoplasm or the neoplastic cells.

The term "subject" as used herein refers to any target of the treatment. Also provided by the present invention is a method of treating neoplastic cells which were grown in tissue culture. Also provided by the present invention is a method of treating neoplastic cells in situ, or in their normal position or location, for example, neoplastic cells of breast or prostate tumors. These in situ neoplasms can be located within or on a wide variety of hosts; for example, human hosts, canine hosts, feline hosts, equine hosts, bovine hosts, porcine hosts, and the like. Any host in which is found a neoplasm or neoplastic cells can be treated and is accordance with the present invention.

The terms "pharmaceutically acceptable", "physiologically tolerable" and grammatical variations thereof, as they refer to compositions, carriers, diluents and reagents, are used interchangeably and represent that the materials are capable of administration to or upon a vertebrate subject without the production of undesirable physiological effects such as nausea, dizziness, gastric upset and the like.

The term "radiation inducible target" is meant to refer to any target molecule, protein, peptide or other substance whose presence in a target tissue is related to the exposure of the target tissue to ionizing radiation. For example, when blood vessels are treated with ionizing radiation, they respond by expressing a number of cell adhesion molecules and receptors that participate in homeostasis. These cell adhesion molecules are thus examples of "radiation inducible targets". Other examples of radiation inducible target molecules in blood vessels include ICAM-1, E-selectin, P-selectin and integrin $\beta_3$. Activated platelets themselves are also radiation inducible targets.

The terms "bind", "binding", "binding activity" and "binding affinity" are believed to have well-understood meanings in the art. To facilitate explanation of the present invention, the terms "bind" and "binding" are meant to refer to protein—protein interactions that are recognized to play a role in many biological processes, such as the binding between an antibody and an antigen. Exemplary protein—protein interactions include, but are not limited to, covalent interactions between side chains, such as disulfide bridges between cysteine residues; hydrophobic interactions between side chains; and hydrogen bonding between side chains.

The terms "binding activity" and "binding affinity" are also meant to refer to the tendency of one protein or polypeptide to bind or not to bind to another protein or polypeptide. The energetics of protein—protein interactions are significant in "binding activity" and "binding affinity" because they define the necessary concentrations of interacting partners, the rates at which these partners are capable of associating, and the relative concentrations of bound and free proteins in a solution.

Following long-standing patent law convention, the terms "a" and "an" mean "one or more" when used in this application, including the claims.

A. General Considerations

Weibel-Palade bodies contain several proteins and proteoglycans that initiate thrombosis and inflammation. These include P-selectin, von Willebrand factor, IL-8 and CD63. To determine whether x-rays produce exocytosis of Weibel-Palade bodies (WPB), the vasculature within the mouse thorax was irradiated and immunohistochemistry for P-selectin was performed. Rapid exocytosis of WPB was observed within 30 minutes of X-irradiation. HUVEC endothelial cells were utilized to study the mechanisms of radiation-mediated WPB exocytosis in vitro. Exocytosis was most efficient at 2 to 5 Gy, whereas higher doses cause apoptosis in endothelial cells which interferes with exocytosis.

P-selectin is a cell adhesion molecule that is sequestered in storage reservoirs within the vascular endothelium and alpha granules in platelets. P-selectin is rapidly translocated to the vascular lumen after tissue injury to initiate the adhesion and activation of platelets and leukocytes. The histologic pattern of P-selectin expression in irradiated tumor blood vessels was studied.

GP-IIb and GP-IIIa are platelet antigens that are not found in the vascular endothelium. Anti-GP-IIb and anti-GP-IIIa antibodies were utilized to determine whether the time-dependent increase in P-selectin staining is due to platelet aggregation. Lewis lung carcinoma tumors in C57BL6 mice were irradiated and stained with anti-GP-IIb and anti-GP-IIIa antibodies. Little GP-IIb or GP-IIIa staining was observed in blood vessels at 1 hour following irradiation. However, GP-IIb and GP-IIIa staining increased at 6 and 24 hours following irradiation. These findings indicate that the increased P-selectin staining within the vascular lumen of irradiated tumors was, in part, due to platelet aggregation.

To verify that platelet aggregation was present in these irradiated blood vessels, tissue sections were stained with anti-GP-IIb and anti-GPIIIa antibodies that stained the platelets. No P-selectin, GP-IIb, or GP-IIIa staining was observed in the brain or kidney, but P-selectin, GP-IIb, and GP-IIIa staining were present in the irradiated lung, intestine and tumor vessels. The P-selectin knockout mouse was used to study the correlation between platelet aggregation (i.e. GPIIb or GP-IIIa accumulation) and P-selectin staining in the vascular endothelium. The GP-IIb and GP-IIIa staining was not localized to the lumen of irradiated blood vessels in the knockout mouse, but extravasated into the irradiated lung, intestine and tumors. Red blood cells also extravasated from irradiated tissues. Therefore, P-selectin accumulation in irradiated blood vessels correlated with maintenance of the barrier function of the endothelium, and knockout of the P-selectin gene leads to extravasation of platelets and red blood cells.

Animal studies using rats demonstrated that P-selectin is localized within the endothelium of tumor blood vessels prior to irradiation. One to six hours following irradiation, P-selectin is mobilized to the lumen of the blood vessel. This is not a tumor or species-specific event. There was no increase in P-selectin staining at 1 Gy but efficient localization occurred with 2, 4, 10 and 20 Gy. P-selectin staining of tumors increased over 24 hours following 10 Gy but not 2 Gy.

The radiation-induced increase in P-selectin was shown to result in platelet aggregation. Immunohistochemical studies using GP-IIb and GP-IIIa revealed the P-selectin is of platelet, not endothelial, origin. Using anti-GP-IIb and anti-GP-IIIa antibodies there was increased staining 6 and 24 hours after radiation. Animal studies using immunofluorescent staining of platelet aggregates demonstrated that radiation-induced platelet aggregation occurs in tissues that express P-selectin such as lung, colon, small intestine and tumors, whereas, it is absent in tissues such as brain, lung and kidney where there is an absence of P-selectin.

Animal studies have also shown that radiation-induced platelet aggregation occurs in tumor cells but not in surrounding P-selectin deficient normal tissue. Therefore, the method of the present invention contemplates the selective targeting of tumors by delivering radiation to target tumors to induce platelet aggregation in tumors and using delivery vehicles which bind activated platelets to carry active agents to the tumor while sparing surrounding normal tissue. In accordance with the present invention, then, the use of radiation to control cellular adhesion molecules involved in tumor growth is a unique approach to the treatment of neoplasms.

To determine whether radiation-induced vascular lumen localization of P-selectin was tumor type-specific or species-specific, tumors in rats, C3H mice, C57BL6 mice, and nude mice were studied. P-selectin localization to the vascular lumen was present in all tumors and all species studied. Irradiated intracranial gliomas showed P-selectin localization to the vascular lumen within one hour, whereas blood vessels in normal brain showed no P-selectin staining in the endothelium and no localization to the irradiated vascular lumen. Thus, radiation-induced localization of P-selectin to the vascular lumen is specific to the microvasculature of malignant gliomas and is not present in blood vessels of the irradiated normal brain. Radiation-induced P-selectin localization to the vascular lumen increased in time-dependent manner, until 24 hours after irradiation. Thus, the method of the present invention is applicable for the delivery of active agents to a broad spectrum of tumor and other neoplastic tissues.

B. Ionizing Radiation Therapy

In accordance with the present invention, ionizing radiation is used to target tissues or cells, such as neoplastic tissues or cells, for selective delivery of an active agent via a delivery vehicle comprising the active agent. Thus, the target tissues or cells are exposed to ionizing radiation, and a delivery vehicle comprising the active agent are administered before, after, during, or combinations thereof, the exposure. Examples of such ionizing radiation include, but are not limited to, gamma rays, X-rays, protons, electrons and alpha particles. Ionizing radiation is commonly used in medical radiotherapy and the specific techniques for such treatment will be apparent to one of ordinary skill in the art.

By way of particular example, the following ionizing radiation dosage ranges are utilized: about 0.1 to about 50 Gy, preferably about 2 to about 30 Gy, more preferably about 4 to about 25 Gy, and still more preferably about 10 to about 20 Gy. Particular dosage amounts include, but are not limited to, 0.4 (or 40 cGY), 1, 2, 4, 10 and 20 Gy.

In an embodiment of the present invention contemplated to be particularly applicable to human subjects, the source of ionizing radiation comprises an external beam photon irradiation source, which is typically utilized at energy levels ranging from about 4 to about 18 MV per photon beam. Appropriate blocks, wedges, and bolus are used to deliver adequate dose to the planned target volume of target tissue. A preferred minimum source-axis distance comprises about 80 cm. The subject receives local-regional irradiation via fields that are designed to encompass sites of disease requiring palliation or primary treatment. All fields are treated daily.

Study, site, treatment intent and normal tissue considerations are also evaluated in the determination of dose. Examples of preferred dosages ranges are as follows. For an ionizing radiation dose that is administered in 1 fraction, a preferred dosage range comprises about 500 to about 1500 cGy, with a preferred dosage range comprising about 800 to about 1200 cGy. For an ionizing radiation dose that is administered in 5 fractions, a preferred dosage range comprises about 1000 to about 3000 cGy, with a preferred dosage range comprising about 1500 to about 2500 cGy, and with a more preferred dosage amount comprising about 2000 cGy. For an ionizing radiation dose that is administered in 10 fractions, a preferred dosage range comprises about 1000 to about 6000 cGy, with a preferred dosage range comprising about 2000 to about 4000 cGy, and with a more preferred dosage amount comprising about 3000 cGy.

For an ionizing radiation dose that is administered in 15 fractions, a preferred dosage range comprises about 1000 to about 7000 cGy, with a preferred dosage range comprising about 2000 to about 5000 cGy, and with a more preferred dosage amount comprising about 3500 cGy. For an ionizing radiation dose that is administered in 30 fractions, a preferred dosage range comprises about 2000 to about 12000 cGy, with a preferred dosage range comprising about 4000 to about 8000 cGy, and with a more preferred dosage amount comprising about 6000 cGy.

C. Delivery Vehicles for Active Agents

Methods for the production of the delivery vehicles comprising active agents in accordance with the present invention are described herein. For example, delivery vehicles, such as cells, peptides, proteins, genetic constructs and antibodies, of the invention can be linked, or operatively attached, to the active agents of the invention by crosslinking or by recombinant DNA techniques.

A delivery vehicle for use in targeted delivery of an active agent is provided in accordance with the present invention. The delivery vehicle comprises a targeting agent that preferentially binds a radiation inducible target in a target tissue. The delivery vehicle can further comprise a carrier. The targeting agent and the carrier can each comprise platelets; leukocytes; a protein; a peptide; an antibody; a microsphere; a liposome; a genetic construct; or combinations thereof. Delivery vehicles of the present invention can be linked, or operatively attached, to the active agents of the invention by crosslinking, by recombinant DNA techniques, or other suitable techniques.

Preferred delivery vehicles preferentially bind activated platelets. More preferably, provided delivery vehicles comprise proteins or peptides which bind activated platelets; antibodies which bind activated platelets; microspheres coated with proteins or peptides which bind activated platelets; liposomes conjugated to proteins or peptides which bind activated platelets, or antibodies which bind activated platelets; and combinations thereof.

Art-recognized bio-compatible particles, such as microspheres or liposomes, are also provided for use as carriers in delivery vehicles. Such particles can be adapted for preferential binding to a radiation inducible target, such as by conjugating, coating or otherwise adhering the particles with or to a peptide or antibody that preferentially binds a radiation inducible target. For example, fibrinogen-coated microspheres (available as thrombospheres from Hemosphere, Inc., Irvine, Calif.) bind to GPIIb/GPIIIa on activated platelets with little binding to the reticular endothelial system (RES) or other organs. These microspheres comprise preferred delivery vehicles and are conjugated to active agents in accordance with techniques described immediately below and in the Examples.

C.1. Protein and Peptide Targeting Agents

A delivery vehicle of the present invention can comprise a protein or peptide targeting agent. Many such proteins or peptides are known in the art, and are provided for use in accordance with the present invention. For example, a peptide sold under the registered trademark APCITIDE® by Diatide, Inc., of Londonderry, N.H. is a peptide that binds to GPIIb/IIIa on activated platelets, as described by Taillefer, J., Nucl. Med. 38:5 (1997).

Fibrinogen preferentially binds activated platelets. Human fibrinogen interacts with binding sites exposed on GPIIb-IIIa of activated platelets through the tentacles present on γ and α chains (Hawiger, J. et al. (1982) Proc. Natl. Acad. Sci. USA 79:2068). The 12-residue carboxyl-terminal segment (SEQ ID NO:1) of the γ chain, encompassing residues 400–411, was pinpointed by Hawiger and others as the platelet receptor recognition domain (Hawiger, J., and Timmons, S. (1992) Methods in Enzymology 215: 228–233.). Hawiger also showed that the sequence—RGD (a95–98) and (a572–575) are involved in the interaction of human fibrinogen α chain with receptors on activated platelets (Hawiger, J. et al. (1989) Biochemistry 28:2909.), but these regions are not essential for fibrinogen binding. Both domains contain the sequence RGD, identified previously as the cell recognition site of fibronectin. The presence of three domains on each half of the fibrinogen molecule, provides preferred conditions for tighter binding of fibrinogen to platelets and for their subsequent aggregation. Fibrinogen and the APCITIDE® peptide thus comprise protein or peptide targeting agents for a delivery vehicle of the present invention.

A preferred protein or peptide delivery vehicle comprises a dodecapeptide HHLGGAKQAGDV (SEQ ID NO:1), the above-noted segment of the γ subunit of fibrinogen, to achieve site-specific binding to irradiated tumors. This peptide segment of the carboxyl terminus of the fibrinogen γ chain binds to GPIIb/IIIa following platelet activation. The amino acid sequence HHLGGAKQAGDV (SEQ ID NO:1) is sufficient for site-specific localization to irradiated tumors.

Thus, protein and polypeptide targeting agents are provided in accordance with the present invention. Additionally, in one embodiment, a polypeptide targeting of the present invention comprises no more than about 100 amino acid residues, preferably no more than about 60 residues, more preferably no more than about 30 residues even more preferably no more than about 10 to 12 residues. Peptides can be linear or cyclic. Thus, it should be understood that a subject polypeptide need not be identical to the amino acid residue sequence of a natural ligand for a radiation inducible target, so long as it includes required binding sequences and is able to target the delivery vehicle in an assay such as is described herein.

A subject polypeptide includes any analog, fragment or chemical derivative of a polypeptide which binds a radiation inducible target. Such a polypeptide can be subject to various changes, substitutions, insertions, and deletions where such changes provide for certain advantages in its use. In this regard, a polypeptide targeting agent of the present invention corresponds to, rather than is identical to, the sequence of a natural ligand for radiation inducible target where one or more changes are made and it retains the ability to bind a radiation inducible target in one or more of the assays as defined herein. Thus, a polypeptide can be in any of a variety of forms of peptide derivatives, that include proteins, amides, conjugates with proteins, cyclized peptides, polymerized peptides, analogs, fragments, chemically modified peptides and proteins, and the like derivatives.

The term "analog" includes chemical analogues (e.g. biAPTICIDE®). Indeed, given the disclosure of the desired binding activity in tissues herein, it is envisioned that chemical compounds (e.g. small molecule mimetics) can be used to provide binding activity in target tissue in accordance with the methods of the present invention. The identification of such compounds is facilitated by the description of assays directed to binding activity in tissues presented herein.

The term "analog" also includes any polypeptide having an amino acid residue sequence substantially identical to a sequence of a natural ligand of radiation inducible target in which one or more residues have been conservatively substituted with a functionally similar residue and which displays the binding activity as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another. Representative substitutions include but are not limited to those presented in SEQ ID NOs:4–9.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as chemical derivatives are those peptides which contain one or more naturally occurring amino acid derivatives of the twenty standard amino acids. For examples: 4-hydroxyproline can be substituted for proline; 5-hydroxylysine can be substituted for lysine; 3-methylhistidine can be substituted for histidine; homoserine can be substituted for serine; and ornithine can be substituted for lysine. Polypeptides of the present invention also include any polypeptide having one or more additions and/or deletions or residues relative to the sequence of a polypeptide whose sequence is shown herein, so long as the requisite activity is maintained. The term "fragment" refers to any subject polypeptide having an amino acid residue sequence shorter than that of a polypeptide disclosed herein.

When a polypeptide of the present invention has a sequence that is not identical to the sequence of an natural ligand of a radiation inducible target, it is typically because one or more conservative or non-conservative substitutions have been made, usually no more than about 30 number percent, and preferably no more than 10 number percent of the amino acid residues are substituted. Additional residues can also be added at either terminus of a polypeptide for the purpose of providing a "linker" by which the polypeptides of the present invention can be conveniently affixed to a label or solid matrix, or carrier. Labels, solid matrices and carriers that can be used with the polypeptides of the present invention are described hereinbelow, including in the Examples.

Amino acid residue linkers are usually at least one residue and can be 40 or more residues, more often 1 to 10 residues, but do not form radiation inducible target ligand epitopes. Typical amino acid residues used for linking are tyrosine, cysteine, lysine, glutamic and aspartic acid, or the like. In addition, a subject polypeptide can differ, unless otherwise specified, from the natural sequence of a radiation inducible target ligand by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases can be present. In this regard, polypeptide cyclization is also a useful terminal modification, and is particularly preferred also because of the stable structures formed by cyclization and in view of the biological activities observed for such cyclic peptides as described herein.

Any peptide of the present invention can be used in the form of a pharmaceutically acceptable salt. Suitable acids which are capable of the peptides with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A peptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W.H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, *Adv Enzymol*, 32:221–96, 1969; Fields et al., *Int. J. Peptide Protein Res.*, 35:161–214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods comprise the sequential addition of one or more amino acid residues or suitably protected amino acid residues to a growing peptide chain. Normally, either the amino or carboxyl group of the first amino acid residue is protected by a suitable, selectively removable protecting group a different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above can be reacted to form their corresponding cyclic peptides. An exemplary method for cyclizing peptides is described by Zimmer et al., *Peptides* 1992, pp. 393–394, ESCOM Science Publishers, B. V., 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

Candidate peptides exhibited desired binding characteristics (i.e. a peptide that bind a radiation inducible target as described herein) can also be identified using a phage peptide library. Random phage peptide libraries, such as T7 and M13 phage libraries are commercially available from Novagen of Madison, Wis., and phage peptide library screening techniques are generally known in the art and are described, for example, in numerous journal articles by E. Ruoslahti.

C.2. Antibodies

Following platelet activation, several antigens are expressed on the surface of platelets. Antibodies are conjugated to radionuclides, cytotoxic agents, gene therapy vectors and liposomes for use as targeting agents in a delivery vehicle of the present invention. Antibody delivery vehicles can be mono-specific, bi-specific or multi-specific. That is, the antibodies can include sites which bind activated platelets and which bind an active agent, such as a gene therapy vector, preferably a viral gene therapy vector. Preferred antibodies comprise anti-P-selectin, anti-GP-IIb, and anti-GP-IIIa antibodies.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin (Ig) molecules, single chain immunoglobulins or antibodies, those portions of an immunoglobulin molecule that contain the paratope, including those portions known in the art as Fab, Fab', F(ab')2 and F(v), and also referred to as antibody fragments.

When an Ig molecule is digested by papain to yield fragments, and these digestion products are dialyzed, protein crystals accounting for one-third of the original protein mass are produced. These crystals are termed the Fc fragment (the complement binding fragment) as they constitute the "fragment crystallizable". Fc, comprising the carboxy-termini of two heavy chains, is dimeric in nature. The heavy chains are held together by inter-chain disulfide bonds. In addition, intra-chain disulfide bonds add to the conformation of the Fc region. Carbohydrates are found attached to the Fc portion of immunoglobulin.

The fragments which account for two-thirds of the original protein mass after papain digest of an Ig bind antigen in a manner equivalent to the original molecule and are termed the Fab fragments as they were antigen binding. Fab fragments are also known as monovalent fragments.

Alternatively, antibody fragments can be prepared by pepsin cleavage, which releases a bivalent antigen-binding $F(ab')_2$ fragment and a complement-binding Fc' fragment. The $F(ab')_2$ fragment can be dissociated by thiol reagents into monovalent fragments. An Fab' fragment is a monovalent fragment prepared from an $F(ab')_2$ fragment.

Provided antibodies can be polyclonal antibodies but are preferably monoclonal antibodies. Preparation techniques for both polyclonal and monoclonal antibodies are well-known in the art and as such, are not discussed in detail herein. See, e.g., Kohler and Milstein, *Nature* 256:495497 (1975); Zola, *Monoclonal Antibodies: a Manual of Techniques*, CRC Press, Inc. (1987). Further, as would be understood by one of ordinary skill in the art, the phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody can therefore contain an antibody molecule having a plurality of antibody combining sites, each immunospecific for a different epitope, e.g., a bispecific monoclonal antibody.

While several suitable techniques for conjugating moieties to peptides and antibodies, in general, are well known in the art (see e.g., U.S. Pat. Nos. 4,340,535 and 5,776,427, and EP 44167, each of which incorporated herein by reference), certain advantages can be achieved through the application of certain preferred technology, both in the preparation of peptide and antibody delivery vehicles comprising active agents and in their purification for subsequent clinical administration. Preferred approaches are disclosed in the Examples. For example, while numerous types of disulfide-bond containing linkers are known which can successfully be employed to conjugate the active agent with the delivery vehicle, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the active agent prior to binding at the site of action.

In cases where a releasable active agent is provided, one desires to have a conjugate that will remain intact under conditions found everywhere in the body except the intended site of action, at which point it is desirable that the conjugate have good "release" characteristics. Therefore, the particular cross-linking scheme, including the particular cross-linking reagent used and the structures that are cross-linked, will be of some significance.

Cross-linking reagents are used to form molecular bridges that tie together functional groups of two different proteins (e.g., a active agent and a delivery vehicle). To link two different proteins in a step-wise manner, heterobifunctional cross-linkers can be used which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker can react with the lysine residue(s) of one protein (e.g., the selected antibody or fragment) and through the thiol reactive group, the cross-linker, already tied up to the first protein, reacts with the cysteine residue (free sulfhydryl group) of the other protein. Useful heterobifunctional crosslinking agents include 4-succinimidyloxycarbonyl-methyl-(2-pyridyldithio)-toluene (SMPT) or N-succinimidyl-3-(2-pyridyidithio)propionate (SPDP), both of which can be obtained from Pierce, Rockland, Ill.

The spacer arm between these two reactive groups of any cross-linkers can have various length and chemical composition. A longer spacer arm allows a better flexibility of the conjugate components while some particular components in the bridge (e.g., benzene group) can lend extra stability to the reactive group or an increased resistance of the chemical link to the action of various aspects (e.g., disulfide bond resistant to reducing agents).

An exemplary cross-linking reagent is SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to its delivery to the site of action by the binding agent. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane (Thorpe et al., *Cancer Res.* 47:5924–5931 (1987)). The use of such cross-linkers is well understood in the art.

Once conjugated, it will be important to purify the conjugate so as to remove contaminants such as unconjugated active agent or delivery vehicle. It is important to remove unconjugated delivery vehicle to reduce undesired toxicity and to avoid the possibility of competition for binding sites in the target tissue between conjugated and unconjugated species. In general, the most preferred purification technique will incorporate the use of a column matrix sold under the registered trademark BLUE-SEPHAROSE® by Pharmacia, Inc., of Piscataway, N.J. with a gel filtration or gel permeation step. The BLUE-SEPHAROSE® column matrix is a column matrix composed of a dye sold under the registered trademark CIBACRON® BLUE 3GA by Ciba Geigy Corporation of Ardsley, N.Y. and agarose, which has been found to be useful in the purification of immunoconjugates (Knowles & Thorpe, *Anal. Biochem.* 120:440–443 (1987)). The use of the BLUE-SEPHAROSE® column matrix combines the properties of ion exchange with active agent binding to provide good separation of conjugated active agent from non-conjugated active agent. The BLUE-SEPHAROSE® column matrix allows the elimination of the free (non-conjugated) delivery vehicle (e.g., the antibody or fragment) from the conjugate preparation. To eliminate the free (non-conjugated) active agent a molecular exclusion chromatography step is preferred using either conventional gel filtration procedure or high performance liquid chromatography.

It is also possible to determine, without undue experimentation, if a monoclonal antibody has the same (i.e., equivalent) specificity (immunoreaction characteristics) as a monoclonal antibody of the present invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides are well known in the art.

The immunospecificity of an antibody, its radiation inducible target binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin that comprises the antibody, and in part by the light chain variable region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention. Thus, the invention contemplates, in one embodiment, a monoclonal antibody of the present invention that is humanized by grafting to introduce components of the human immune system without substantially interfering with the ability of the antibody to bind antigen. Humanized antibodies can also be produced using animals engineering to produce humanized antibodies, such as those available from Medarex of Annandale, N.J. (mice) and Abgenix, Inc., of Fremont, Calif. (mice).

The use of a molecular cloning approach to generate antibodies, particularly monoclonal antibodies, and more particularly single chain monoclonal antibodies, is also contemplated. The production of single chain antibodies has been described in the art, see e.g., U.S. Pat. No. 5,260,203, the contents of which are herein incorporated by reference. For this, combinatorial immunoglobulin phagemid or phage-displayed libraries are prepared from RNA isolated from the spleen of the immunized animal, and phagemids expressing appropriate antibodies are selected by panning on endothelial tissue. This approach can also be used to prepared humanized antibodies. The advantages of this approach over conventional hybridoma techniques are that approximately $10^4$ times as many antibodies can be produced and screened in a single round, and that new specificities are generated by H and L chain combination in a single chain, which further increases the chance of finding appropriate antibodies. Thus, an antibody of the present invention, or a "derivative" of an antibody of the present invention pertains to a single polypeptide chain binding molecule which has binding specificity and affinity substantially similar to the binding specificity and affinity of the light and heavy chain aggregate variable region of an antibody described herein.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in *The Pharmacology of Monoclonal Antibodies*, vol. 113, Rosenburg and Moore eds., Springer-Verlag, New York, pp. 269–315 (1994).

Using a phage-displayed approach for the production of antibodies, scFv antibody clones that bind to a radiation inducible target are identified by competing off those phage displayed antibodies using another monoclonal antibody disclosed herein. Fv regions are sequenced and bivalent functional reagents are designed and tested in an assay disclosed herein below. Thus, a preferred source for an antibody, or derivative or fragment thereof, is a recombinant phage-displayed antibody library. The recombinant phage can comprise antibody encoding nucleic acids isolated from any suitable vertebrate species, including mammalian species such as mouse and rat; but preferably comprises antibody encoding nucleic acids isolated from human. Such antibodies are thus already "humanized".

C.3. Recombinant DNA Techniques

Alternatively, one might find that the application of recombinant DNA technology to the active agent moiety will provide additional significant benefits in accordance the invention. For example, the cloning and expression of active agent candidates, particularly toxin candidates, has now been described through the publications of others (O'Hare et al., *FEBS Lett* 210:731 (1987); Lamb et al., *Eur Jrnl Biochem* 148:265–270 (1985); Hailing et al., *Nucl Acids Res* 13:8019–8033 (1985)), it is now possible to identify and prepare smaller or otherwise variant peptides which nevertheless exhibit an appropriate active agent activity. Moreover, the use of cloned active agent candidates allows the application of site-directed mutagenesis, through which one can readily prepare and screen for mutated peptides and obtain additional useful moieties for use in connection with the present invention. Genetic constructs that express active agents, such as vectors and preferably viral vectors, can be engineered to express a targeting agent such as in a protein coat, as disclosed in Example 12.

Standard recombinant DNA techniques that are well known to those of skill in the art can be utilized to express nucleic acids encoding the delivery vehicle/active agent compounds of the invention. These methods include, for example, in vitro recombinant DNA techniques, synthetic techniques and in vivo recombination/genetic recombination. DNA and RNA synthesis can, additionally, be performed using an automated synthesizers (see, for example, the techniques described in Sambrook et al., *Molecular Cloning, A Laboratory Manual*, Cold Spring Harbor Laboratory, N.Y. (1989); and Ausubel et al., *Current Protocols in Molecular Biology*, Greene Publishing Associates and Wiley Interscience, N.Y. (1989).

When produced via recombinant DNA techniques such as those described herein, the delivery vehicle/active agent compounds of the invention can be referred to herein as "fusion proteins". It is to be understood that such fusion proteins contain at least a delivery vehicle and an active agent operatively attached, such that the fusion protein can be used in accordance with the methods of the present invention. The fusion proteins can also include additional peptide sequences, such as peptide spacers which operatively attach the delivery vehicle and active agent, as long as such additional sequences do not appreciably affect the delivery or active agent activities of the fusion protein.

Fusion proteins or polypeptides and nucleic acids the same which have functionally equivalent codons are also covered by the present invention. The term "functionally equivalent codon" is used herein to refer to codons that encode the same amino acid, such as the six codons for arginine or serine, and also to refer to codons that encode biologically equivalent amino acids (see Table 2).

TABLE 2

Functionally Equivalent Codons.

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Praline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences can include additional residues, such as additional N- or C-terminal amino acids or 5' or 3' sequences, and yet still be essentially as set forth in one of the sequences disclosed herein, so long as the sequence meets the criteria set forth above, including the maintenance of binding activity. The addition of terminal sequences particularly applies to nucleic acid sequences which can, for example, include various non-coding sequences flanking either of the 5' or 3' portions of the coding region or can include various internal sequences, i.e., introns, which are known to occur within genes.

Depending on the specific active agent used as part of the fusion protein, it might be necessary to provide a peptide spacer operatively attaching the delivery vehicle and the active agent compound which is capable of folding into a disulfide-bonded loop structure. Proteolytic cleavage within the loop would then yield a heterodimeric polypeptide wherein the delivery vehicle and the active agent compound are linked by only a single disulfide bond. See e.g., Lord et al., in *Genetically Engineered Active Agents* (Ed. A. Frank, M. Dekker Publ., p. 183) (1992). An example of such a active agent is a Ricin A-chain toxin.

When certain other active agents are utilized, a non-cleavable peptide spacer can be provided to operatively attach the delivery vehicle and the active agent of the fusion protein. Active agents which can be used in conjunction with non-cleavable peptide spacers are those which can, themselves, be converted by proteolytic cleavage, into a cytotoxic disulfide-bonded form (see e.g., Ogata et al., *J. Biol. Chem.* 256:20678–20685 (1990)). An example of such an active agent is a *Pseudomonas* exotoxin compound.

Nucleic acids that can be utilized herein comprise nucleic acid sequences that encode a delivery vehicle of interest and nucleic acid sequences that encode a active agent of interest. Such delivery vehicle-encoding and active agent-encoding nucleic acid sequences are attached in a manner such that translation of the nucleic acid yields the delivery vehicle/active agent composition of the invention.

Standard techniques, such as those described above can be used to vconstruct expression vectors containing the above-described nucleic acids and appropriate transcriptional/translational control sequences. A variety of host-expression vector systems can be utilized. These include but are not limited to microorganisms such as bacteria (e.g., *E. coli, B. subtilis*) transformed with recombinant bacteriophage DNA, plasmid DNA or cosmid DNA expression vectors containing delivery vehicle/active agent coding sequences; yeast (e.g., *Saccharomyces, Pichia*) transformed with recombinant yeast expression vectors containing delivery vehicle/active agent coding sequences; insect cell systems infected with recombinant virus expression vectors (e.g., baculovirus) containing the delivery vehicle/active agent coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the delivery vehicle/active agent coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter; lentiviral vectors).

In bacterial systems a number of expression vectors can be advantageously selected depending upon the use intended for the delivery vehicle/active agent being expressed. For example, when large quantities of delivery vehicle/active agent are to be produced for the generation of antibodies or to screen peptide libraries, vectors which direct the expression of high levels of fusion protein products that are readily purified can be desirable. Such vectors include but are not limited to the *E. coli* expression vector pUR278 (Ruther et al., *EMBO J.* 2:1791 (1983)), in which the delivery vehicle/active agent coding sequence can be ligated individually into the vector in frame with the lac Z coding region so that a fusion protein additionally containing a portion of the lac Z product is provided; pIN vectors (Inouye et al., *Nucleic Acids Res.* 13:3101–3109 (1985); Van Heeke et al., *J. Biol. Chem.* 264:5503–5509 (1989)); and the like. pGEX vectors can also be used to express foreign polypeptides, such as the delivery vehicle/active agents as fusion proteins additionally containing glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the delivery vehicle/active agent protein of the fusion protein can be released from the GST moiety.

In an insect system, *Autograph californica* nuclear polyhidrosis virus (AcNPV) is used as a vector to express foreign genes. The virus grows in *Spodoptera frugiperda* cells. The delivery vehicle/active agent coding sequences can be cloned into non-essential regions (for example the polyhedrin gene) of the virus and placed under control of an AcNPV promoter (for example the polyhedrin promoter). Successful insertion of the delivery vehicle/active agent coding sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (see e.g., Smith et al., *J. Virol.* 46:584 (1983); U.S. Pat. No. 4,215,051).

In mammalian host cells, a number of viral based expression systems can be utilized. In cases where an adenovirus is used as an expression vector, the delivery vehicle/active agent coding sequences can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing delivery vehicle/active agent proteins in infected hosts (see e.g., Logan et al., *Proc. Natl. Acad. Sci. USA* 81:3655–3659 (1984)). Specific initiation signals can also be required for efficient translation of inserted delivery vehicle/active agent coding sequences. These signals include the ATG initiation codon and adjacent sequences. Exogenous translational control signals, including the ATG initiation codon, can additionally need to be provided. One of ordinary skill in the art would readily be capable of determining this and providing the necessary signals. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., *Methods in Enzymol.* 153:516–544 (1987)).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, etc. For long-term, high-yield production of recombinant proteins, stable expression is preferred. For example, cell lines which stably express constructs encoding the delivery vehicle/active agent compounds can be engineered. Rather than using expression vectors which contain viral origins of replication, host cells can be transformed with delivery vehicle/active agent DNA controlled by appropriate expression control elements (e.g., promoter, enhancer, sequences, transcription terminators, polyadenylation sites, etc.), and a selectable marker. Following the introduction of foreign DNA, engineered cells can be allowed to grow for 1 or 2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems can be used, including, but not limited, to the herpes simplex virus thymidine kinase (Wigler et al., *Cell* 11:223 (1977)), hypoxanthine-guanine phosphoriboxyltransferase (Szybalska et al., *Proc. Natl. Acad. Sci. USA* 48:2026 (1962)), and adenine phosphoribosyltransferase genes (Lowy et al., *Cell* 22:817 (1980)) can be employed in tk-, hgprt- or aprt-cells, respectively. Also, antimetabolite resistance can be used as the basis of selection for dhfr, which confers resistance to methotrexate (Wigler et al., *Proc. Nat. Acad. Sci. USA* 77:3567 (1980); O'Hare et al., *Proc. Natl. Acad. Sci. USA* 78:1527 (1981)); gpt, which confers resistance to mycophenolic acid (Mulligan et al., *Proc Natl Acad Sci USA* 78:2072 (1981)); neo, which confers resistance to the aminoglycoside G-418 (Colberre-Garapin et al., *J Mol Biol* 150:1 (1981)); and hygro, which confers resistance to hygromycin (Santerre et al., *Gene* 30:147 (1984)).

Some of the therapeutic applications of the present invention involve the targeting of an active agent moiety to the endothelium, particularly tumor endothelium. This is due to the much greater ability of most active agents to deliver a cell killing effect as compared to other potential agents. However, there can be circumstances, such as when the target antigen does not internalize by a route consistent with efficient intoxication by delivery vehicle/active agent compounds, such as immunotoxins, where one will desire to target chemotherapeutic agents such as antitumor drugs, other cytokines, antimetabolites, alkylating agents, hormones, and the like. The advantages of these agents over their non-delivery vehicle conjugated counterparts is the added selectivity afforded by the delivery vehicle, such as an antibody. Exemplary agents include, but are not limited to, steroids, cytosine arabinoside, methotrexate, aminopterin, anthracyclines, mitomycin C, vinca alkaloids, demecolcine, etoposide, mithramycin, and the like. This list is, of course, merely exemplary in that the technology for attaching pharmaceutical agents to delivery vehicles, such as peptides or to antibodies, for specific delivery to tissues is well established.

The technology for attaching paramagnetic, radioactive and even fluorogenic ions to delivery vehicles, such as peptides and antibodies, is well established. Many of these methods involve the use of a metal chelate complex employing, for example, an organic chelating agent such a DTPA attached to the peptide or to the antibody. See e.g., U.S. Pat. No. 4,472,509. In the context of the present invention the selected ion is thus targeted to the target tissue by the delivery vehicle, such as a peptide or an antibody, allowing therapy or imaging to proceed by means of the attached ion.

A variety of chemotherapeutic and other pharmacologic agents have now been successfully conjugated to peptides and to antibodies and shown to function pharmacologically (see e.g., Vaickus et al., *Cancer Invest* 9:195–209 (1991)). Exemplary antineoplastic agents that have been investigated include doxorubicin, daunomycin, methotrexate, vinblastine, and various others. Dillman et al., *Antibody Immunocon Radiopharm* 1:65–77 (1988); Pietersz et al., *Antibody Immunoconj Radiopharm* 1:79–103 (1988). Moreover, the attachment of other agents such as neocarzinostatin (Kimura et al., *Immunogenetics* 11:373–381 (1980)), macromycin, trenimon (Ghose et al., *Meth. Enzymology* 93:280–333 (1983)) and α-amanitin has been described.

In addition to chemotherapeutic agents, the invention is applicable to the specific delivery of a wide variety of other agents to tumor vasculature. For example, under certain circumstances, one can desire to deliver a coagulant such as Russell's Viper Venom, activated Factor IX, activated Factor X or thrombin to the tumor vasculature. This will result in coagulation of the tumor's blood supply. One can also envisage targeting a cell surface lytic agent such as phospholipase C, (Flickinger & Trost, *Eu. J. Cancer* 12(2):159–60 (1976)) or cobra venom factor (CVF) (Vogel & Muller-Eberhard, *Anal. Biochem* 118(2):262–268 (1981)) which should lyse the tumor endothelial cells directly. The operative attachment of such structures to delivery vehicles, such as peptides and antibodies, can be readily accomplished, for example, by protein—protein coupling agents such as SMPT. Moreover, one can desire to use growth factors, other cytokines or even bacterial endotoxin or the lipid A moiety of bacterial endotoxin as active agents, in order, e.g., to achieve modulation of cytokine release. The attachment of such substances to peptide and antibody delivery vehicles is again well within the skill in the art as exemplified by Ghose et al., *CRC Critical Reviews in Therapeutic Drug Carrier Systems* 3:262–359 (1987).

Thus, it is generally believed to be possible to conjugate to peptides and antibodies any active agent that has a primary or secondary amine group, hydrazide or hydrazine group, carboxyl alcohol, phosphate, or alkylating group available for binding or cross-linking to the amino acids or carbohydrate groups of the peptide or antibody. In the case of protein structures, this is most readily achieved by means of a cross linking agent as described above. In the case of doxorubicin and daunomycin, attachment can be achieved by means of an acid labile acyl hydrazone or cis aconityl linkage between the drug and the peptide or antibody. Finally, in the case of methotrexate or aminopterin, attachment is achieved through a peptide spacer such as L-Leu-L-Ala-L-Leu-L-Ala, between the y-carboxyl group of the drug and an amino acid of the peptide or antibody.

Alternatively, any such structures which are nucleic acid-encoded structures can be operatively attached to the delivery vehicles of the invention by standard recombinant DNA techniques, such as, for example, those discussed above.

In accordance with another embodiment of the present invention, platelets are used as delivery vehicles for the selective delivery of active agents to a target tissue in a vertebrate subject. Platelets are loaded or labeled with an active agent or agents in accordance with art-recognized techniques, such as those described in U.S. Pat. Nos. 5,292,524 and 5,328,840, the entire contents of each of which herein incorporated by reference. Other techniques, including electroporation, for loading or labeling platelets for use in accordance with the present invention are described in the Examples presented herein below.

As used herein, the term "loading" refers to the incorporation of material inside a delivery vehicle, such as a platelet. The incorporated material can be located, for example, within the cytoplasm of the platelet or be compartmentalized within a vacuole or organelle. The material can be taken up or "loaded" into the platelet by a variety of processes, such as, for example, phagocytosis, membrane fusion or receptor-mediated endocytosis. The pathway by which material is taken up is not critical so long as the material to be incorporated inside a platelet successfully crosses the platelet cell membrane. As would be apparent to one of ordinary skill in the art, active agents can be loaded directly into platelets or can be loaded via a carrier, such as a liposome or hapten. Haptens can be employed, for example, to conjugate radionuclides to peptides (e.g. $^{99}$Tc conjugated to fibrinogen) by use of techniques described by Griffiths, G. L., et al. (1994a) *Cancer* 73 Supplement and by Griffiths, G. L., et al. (1994b) *Nuclear Medical Biology* 2:649–655.

As disclosed in the Examples presented herein below, leukocytes bind activated platelets, and as such, are provided for use as delivery vehicles in accordance with the present invention. Leukocytes are loaded with active agent using the techniques described above with respect to the conjugation of active agents to peptide and antibody delivery vehicles and with respect to the loading of platelets, by electroporation or by phagocytosis, membrane fusion or receptor-mediated endocytosis. For example, leukocytes can be loaded by conjugating with a viral gene therapy vector to a platelet binding P-selectin counter receptor (PGSL) on the surface of the leukocyte using the conjugation techniques disclosed herein above.

C.4. Delivery Vehicles Comprising Liposomes as Carriers

In one embodiment, a delivery vehicle of the present invention comprises a liposome. Thus, a liposome comprises a preferred carrier. The term "liposome" is meant its art recognized meaning to a particle having one or more encapsulating membranes formed by amphiphilic molecules (such as lipids for example) and in particular particles having a bilayer membrane and an enclosed aqueous core, are versatile carriers for the site specific delivery of therapeutic and diagnostic agents. Active targeting to specific organs or tissues can be achieved by incorporation of lipids with attached thereto a targeting agent as disclosed herein. An active agent can also be incorporated into a liposome delivery vehicle of the present invention as disclosed herein. Optionally, the targeting agent and/or the active agent is not releasably attached to the liposome delivery vehicle; that is, the liposome delivery vehicle is free of a releasably attached active agent and/or target agent.

The liposomes themselves are spherical vesicles having a lipid layer surrounding a central space. The present invention is particularly concerned with unilammellar and multi-lamellar liposomes which respectively have a single lipid bilayer or multiple lipid bilayers surrounding an aqueous core. Liposomes spontaneously form upon dispersion of lipids, particularly phospholipids, in aqueous media and the liposomal structure of the agents of the invention can be produced by conventional techniques. Such conventional techniques are referred to in WO92/21017 (Unger) and by Papahadjopolous in *Ann Rep. Med. Chem.* 14: 250–260 (1979) and include reverse evaporation, freeze-thaw, detergent dialysis, homogenization, sonication, microemulsification and spontaneous formation upon hydration of a dry lipid film. Multi-lamellar liposomes can be used according to the invention or can be converted to liposomes with lower lamellarity, or to unilamellar liposomes, by known methods. Unilamellar liposomes can also be prepared directly.

Liposome preparations are typically heterogeneous in size and the liposomes used according to the invention can be sized to the desired diameter by known techniques, eg. extrusion, freeze-thaw, mechanical fragmentation, homogenization and sonication. The liposomes used according to the invention are advantageously 20–5000 nm diameter, unilamellar or multi-lamellar. The liposomes can be lyophilized to increase shelf life and lyophilized liposomes can be reconstituted by vigorous shaking with aqueous buffer prior to use. Formulations can include agents which serve to stabilize the liposomal material for the lyophilization procedure. Liposomes smaller than 200 nm can be sterilized after formulation by filtration through a 0.2 μm filter.

The lipids used as the liposomal membrane forming molecules are typically phospholipids or hydrogenated phospholipids such as natural or synthetic phosphatidylcholines (lecithins) (PC), phosphatidylethanolamines (PE), lysolecithins, lysophosphatidylethanolamines, phosphatidylserines (PS), phosphatidylglycerols (PG), phosphatidylinositol (PI), sphingomyelins, cardiolipin, phosphatidic acids (PA), fatty acids, gangliosides, glucolipids, glycolipids, mono-, di or triglycerides, ceramides or cerebrosides, eg. liposome membrane forming compounds such as are described in WO-92/21017.

The membrane forming lipids can also comprise polymerizable lipids, eg. methacrylate lipids, thiol and disulphide lipids, dienoate lipids, styryl lipids and diacetylanic lipids as described by Johnston in *Liposome Technology* Vol. I, Gregoriades Ed., pages 123–129 (1983) and Singh in *Phospholipid Handbook*, Cevc Ed., Dekker, pages 233–291 (1993) and references therein. The use of polymerizable lipids in the formation of the liposomes provides one route for increasing liposome stability.

The lipids forming the bilayer vesicle, i.e., liposome, can also be cationic lipids, which have a lipophilic moiety, such as a sterol, an acyl or diacyl chain, and where the lipid has an overall net positive charge. Preferably, the head group of the lipid carries the positive charge. Exemplary cationic lipids include 1,2-d ioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3β[N-(N',N'-dimethylaminoethane)carbamoly] cholesterol (DC-Chol); and dimethyldioctadecylammonium (DDAB).

The cationic vesicle-forming lipid can also be a neutral lipid, such as dioleoylphosphatidyl ethanolamine (DOPE), cholesterol-containing DOPC, or an amphipathic lipid, such as a phospholipid, derivatized with a cationic lipid, such as polylysine or other polyamine lipids. For example, the neutral lipid (DOPE) can be derivatized with polylysine to form a cationic lipid.

The liposomal membrane can also have steroids and other compounds incorporated into it, eg. to affect the biodistribution of the liposome. Suitable steroids include for example cholesterol, cholesterol derivatives, cholestane, cholic acid, and bile acids, but particularly cholesterol. The inclusion of steroids serves to modify the fluidity of the liposome membrane and this affects biodistribution. Thus higher transition temperature lipids lead to longer blood half lives and the inclusion of cholesterol results in a more rigid and less permeable bilayer. A decrease in RES-uptake is observed with the addition of cholesterol.

The biodistribution modifiers can be incorporated by the use of a phospholipid derivative having a pendant biodistribution modifying function, by the use of a biodistribution modifying agent having a hydrophobic "anchor" moiety which associates with the liposomal membrane or by coupling a biodistribution modifier to an anchor molecule present in the liposomal membrane. Particularly preferred biodistribution modifiers include compounds, especially amphiphilic polymers, which serve to reduce in vivo protein binding to the liposome and thus prolong the half life of the liposomes in the blood. Polyalkyleneoxy polymers, such as polethylene glycol (PEG) and gangliosides, such as $Gm_1$, are effective in this regard. Incorporation of 1–10%, relative to the weight of liposome membrane forming material, of PEG-PE derivatives significantly thus extends blood half life. Liposomes prepared from perfluorinated phospholipids (see Santaella, FEBS Letters 336:481–484 (1993) and Angew, Chem. Int. Ed. Eng. 30: 567–568 (1991)) can also extend blood half-lives.

Hydrophilic polymers suitable for use in a polymer coating include polyvinylpyrrolidone, polyvinylmethylether, polymethyloxazoline, polyethyloxazoline, polyhydroxypropyl oxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide. In a preferred embodiment, the hydrophilic polymer is polyethyleneglycol (PEG), preferably as a PEG chain having a molecular weight between 500–10,000 daltons, more preferably between 2,000–10,000 daltons and most preferably between 1,000–5,000 daltons.

Liposome biodistribution is also significantly dependent upon surface charge and the liposomes according to the invention can desirably include 1 to 10%, relative to the weight of liposome membrane forming material, of negatively charged phospholipids such as for example phosphatidylserine, phosphatidylglycerols, phosphatidic acids, and phosphatidylinositol. To produce the contrast media compositions of the invention, the liposomes are formulated in physiologically tolerable liquid carrier medium, eg. an aqueous solution which can include one or more additives, such as pH modifying agents, chelating agents, antioxidants, tonicity modifying agents, cryoprotectants, further contrast agents, etc.

Examples of suitable ingredients to adjust the pH, include physiologically tolerable acids, bases and buffers, such as acetic acid, citric acid, fumaric acid, hydrochloric acid, malic acid, phosphoric acid, sulfuric acid, or tartaric acid, ammonia, ammonium carbonate, diethanolamine, diisopropanolamine, potassium hydroxide, sodium bicarbonate, sodium borate, sodium carbonate, sodium hydroxide, trolamine, ammonium phosphate, boric acid, citric acid, lactic acid, potassium metaphosphate, potassium phosphate monobasic, sodium acetate, sodium biphosphate, sodium citrate, sodium lactate, sodium phosphate, Tris, and N-methyl glucamine. Examples of suitable chelating agents include EDTA, DTPA, DTPA-BMA and salts and complexes thereof especially calcium, sodium or meglumine salts, e.g. edetate disodium, edetic acid, calcium EDTA.

Examples of suitable anti-oxidants include ascorbic acid, ascorbyl palmitate, cysteine, monothioglycerol, butylated hydroxyanisole, butylated hydroxytoluene, hypophosphoric acid, propyl gallate, sodium bisulfate, sodium formaldehyde sulfoxylate, sodium metabisulfate, sodium thiosulfate, sulfur dioxide, or tocopherol. Examples of suitable tonicity agents, include sodium chloride, glucose, sucrose, mannitol, sorbitol and dextrose. These agents preferably are used to make the formulation isotonic or near isotonic with blood.

Examples of suitable anti-microbial agents include, benzalkonium chloride, benzyl alcohol, chlorobutanol, meta-cresol, methyl p-hydroxybenzoate, propyl p-hydroxybenzoate, and timerosal. Examples of suitable cryoprotectants, agents which aid in the lyophilization and reconstitution processes include sodium chloride, sorbitol, mannitol, glucose and polyethyleneglycol.

Representative starting materials and method for the preparation of liposomes are also disclosed in U.S. Pat. Nos. 6,048,546; 6,045,821; 6,045,822; and 6,043,094. The entire contents of each of these U.S. patents are incorporated by reference herein.

D. Active Agents

As described hereinabove, the active agent can comprise a therapeutic or an imaging agent. The therapeutic agent can comprise chemotherapeutic agents, toxins, radiotherapeutics, or radiosensitizing agents. Each agent is loaded in a total amount effective to accomplish the desired result in the target tissue, whether the desired result be imaging the target tissue or treating the target tissue.

Chemotherapeutics useful as active agents in loaded platelets are typically small chemical entities produced by chemical synthesis. Chemotherapeutics include cytotoxic and cytostatic drugs. Chemotherapeutics can include those which have other effects on cells such as reversal of the transformed state to a differentiated state or those which inhibit cell replication. Exemplary chemotherapeutic agents include, but are not limited to, anti-tumor drugs, cytokines, anti-metabolites, alkylating agents, hormones, and the like.

Additional examples of chemotherapeutics include common cytotoxic or cytostatic drugs such as for example: methotrexate (amethopterin), doxorubicin (adrimycin), daunorubicin, cytosine arabinoside, etoposide, 5–4 fluorouracil, melphalan, chlorambucil, and other nitrogen mustards (e.g. cyclophosphamide), cis-platinum, vindesine (and other vinca alkaloids), mitomycin and bleomycin. Other chemotherapeutics include: purothionin (barley flour oligopeptide), macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin and the like. Certainly, the use of combinations of chemotherapeutic agents is also provided in accordance with the present invention.

Toxins are useful as active agents. When a toxin is loaded into a platelet, the toxin-loaded platelet is specifically delivered to a target tissue by way of exposure of the target tissue to ionizing radiation, and the toxin moiety kills cells in the tissue. Toxins are generally complex toxic products of various organisms including bacteria, plants, etc.

Exemplary toxins include, but are not limited to, coagulants such as Russell's Viper Venom, activated Factor IX, activated Factor X or thrombin; and cell surface lytic agents such as phospholipase C, (Flickinger & Trost, Eu. *J. Cancer* 12(2):159–60 (1976)) or cobra venom factor (CVF) (Vogel & Muller-Eberhard, *Anal. Biochem* 118(2):262–268 (1981)) which should lyse neoplastic cells directly. Additional examples of toxins include but are not limited to: ricin, ricin A chain (ricin toxin), *Pseudomonas* exotoxin (PE), diphtheria toxin (DT), bovine pancreatic ribonuclease (BPR), pokeweed antiviral protein (PAP), abrin, abrin A chain (abrin toxin), gelonin (GEL), saporin (SAP), modeccin, viscumin and volkensin.

Exemplary radiotherapeutic agents include, but are not limited to, $^{47}$Sc, $^{67}$Cu, $^{90}$Y, $^{109}$Pd, $^{123}$I, $^{125}$I, $^{131}$I, $^{111}$In, $^{186}$Re, $^{188}$Re, 199Au, $^{211}$At, $^{212}$Pb and $^{212}$Bi. Other radionuclides which have been used by those having ordinary skill in the art include: $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$CS, $^{143}$Pr, $^{161}$Tb, $^{177}$Lu, $^{191}$Os, $^{193M}$Pt, $^{197}$Hg, all beta negative and/or auger emitters. Some preferred radionuclides include: $^{90}$Y, $^{131}$I, $^{211}$At and $^{212}$Pb/$^{212}$Bi.

Radiosensitizing agents are substances that increase the sensitivity of cells to radiation. Exemplary radiosensitizing agents include, but are not limited to, nitroimidazoles, metronidazole and misonidazole (see DeVita, V. T. Jr. in *Harrison's Principles of Internal Medicine*, p. 68, McGraw-Hill Book Co., N.Y. 1983, which is incorporated herein by reference), as well as art-recognized boron-neutron capture and uranium capture systems. See, e.g., Gabe, D. *Radiotherapy & Oncology* 30:199–205 (1994); Hainfeld, *J. Proc. Natl. Acad. Sci. USA* 89:11064–11068 (1992). A delivery vehicle comprising a radiosensitizing agent as the active moiety is administered and localizes at the target tissue. Upon exposure of the tissue to radiation, the radiosensitizing agent is "excited" and causes the death of the cell.

Radiosensitizing agents are also substances which become more toxic to a cell after exposure of the cell to ionizing radiation. In this case, DNA protein kinase (PK) inhibitors, such as R106 and R116 (ICOS, Inc.); tyrosine kinase inhibitors, such as SU5416 and SU6668 (Sugen Inc.); antiangiogenesis agents and inhibitors of DNA repair enzymes comprise examples.

Another provided radiosensitizing agent comprises a genetic construct which comprises an enhancer-promoter region which is responsive to radiation, and at least one structural gene whose expression is controlled by the enhancer-promoter. In accordance with the present invention, methods of destroying, altering, or inactivating cells in target tissue by delivering the genetic constructs to the cells of the tissues via delivery vehicles and inducing expression of the structural gene or genes in the construct by exposing the tissues to ionizing radiation are also provided. Such genetic constructs are loaded, conjugated or otherwise linked with a delivery vehicle in accordance with art-recognized techniques, such as electroporation and as are described herein above. Exemplary genetic constructs and related techniques are described in U.S. Pat. Nos. 5,817,636; 5,770,581; 5,641,755; and 5,612,318, the entire contents of each of which herein incorporated by reference. Additionally, the recombinant DNA techniques described hereinabove are applicable to the preparation of genetic construct active agents.

Exemplary imaging agents include, but are not limited to, paramagnetic, radioactive and fluorogenic ions. Preferably, the imaging agent comprises a radioactive imaging agent. Exemplary radioactive imaging agents include, but are not limited to, gamma-emitters, positron-emitters and x-ray-emitters. Particular radioactive imaging agents include, but are not limited to, $^{43}$K, $^{52}$Fe, $^{57}$Co, $^{67}$Cu, $^{67}$Ga, $^{68}$Ga, $^{77}$Br, $^{81}$Rb/$^{81M}$MKr, $^{87m}$Sr, $^{99m}$Tc, $^{111}$In, $^{113}$In, 123I, 125I, $^{127}$Cs, $^{129}$Cs, $^{131}$I, $^{132}$I, $^{197}$Hg, $^{203}$Pb and $^{206}$Bi. Other radioactive imaging agents known by one skilled in the art can be used as well.

D. Dosages for Active Agents

Because delivery vehicles are specifically targeted to irradiated cells, a delivery vehicle which comprises an active agent is administered in a dose less than that which is used when the active agent is administered directly to a subject, preferably in doses that contain up to about 100 times less active agent. In some embodiments, delivery vehicles which comprise an active agent are administered in doses that contain about 10 to about 100 times less active agent as an active moiety than the dosage of active agent administered directly. To determine the appropriate dose, the amount of compound is preferably measured in moles instead of by weight. In that way, the variable weight of delivery vehicles does not affect the calculation. A one to one ratio of delivery vehicle to active agent in the delivery vehicles of the present invention is presumed.

Typically, chemotherapeutic conjugates are administered intravenously in multiple divided doses. Up to 20 gm IV/dose of methotrexate is typically administered. When methotrexate is administered as the active moiety in a delivery vehicle of the invention, there is about a 10- to 100-fold dose reduction. Thus, presuming each delivery vehicle includes one molecule of methotrexate to one mole of delivery vehicle, of the total amount of delivery vehicle active agent administered, up to about 0.2 to about 2.0 g of methotrexate is present and therefore administered. In some embodiments, of the total amount of delivery vehicle/active agent administered, up to about 200 mg to about 2 g of methotrexate is present and therefore administered.

By way of further example, doxorubicin and daunorubicin each weigh about 535. Presuming each delivery vehicle includes one molecule of doxorubicin or daunorubicin to one delivery vehicle, a provided dose range for delivery vehicle-doxorubicin vehicle or delivery vehicle-daunorubicin is between about 40 to about 4000 mg. In some embodiments, dosages of about 100 to about 1000 mg of delivery vehicle-doxorubicin or delivery vehicle-daunorubicin are administered. In some embodiments, dosages of about 200 to about 600 mg of delivery vehicle-doxorubicin or delivery vehicle-daunorubicin are administered.

Toxin-containing loaded delivery vehicles are formulated for intravenous administration. Using an intravenous approach, up to 6 nanomoles/kg of body weight of toxin alone have been administered as a single dose with marked therapeutic effects in patients with melanoma (Spitler L. E., et al. (1987) *Cancer Res.* 47:1717). In some embodiments of the present invention, then, up to about 11 micrograms of delivery vehicle-toxin/kg of body weight can be administered for therapy.

The molecular weight of ricin toxin A chain is 32,000. Thus, for example, presuming each delivery vehicle includes one molecule of ricin toxin A chain to one delivery vehicle, delivery vehicles comprising ricin toxin A chain are administered in doses in which the proportion by weight of ricin toxin A chain is about 1 to about 500 μg of the total weight of the administered dose. In some preferred embodiments, delivery vehicles comprising ricin toxin A chain are administered in doses in which the proportion by weight of ricin toxin A chain is about 10 to about 100 μg of the total weight of the administered dose. In some preferred embodiments, delivery vehicles comprising ricin toxin A chain are administered in doses in which the proportion by weight of ricin toxin A chain is about 2 to about 50 μg of the total weight of the administered dose.

The molecular weight of diphtheria toxin A chain is 66,600. Thus, presuming each delivery vehicle includes one molecule of diphtheria toxin A chain to one delivery vehicle, delivery vehicles comprising diphtheria toxin A chain are administered in doses in which the proportion by weight of diphtheria toxin A chain is about 1 to about 500 μg of the total weight of the administered dose. In some preferred embodiments, delivery vehicles comprising diphtheria toxin A chain are administered in doses in which the proportion by weight of diphtheria toxin A chain is about 10 to about 100 μg of the total weight of the administered dose. In some preferred embodiments, delivery vehicles comprising diphtheria toxin A chain are administered in doses in which the proportion by weight of diphtheria toxin A chain is about 40 to about 80 μg of the total weight of the administered dose.

The molecular weight of *Pseudomonas* exotoxin is 22,000. Thus, presuming each delivery vehicle includes one molecule of *Pseudomonas* exotoxin to one delivery vehicle, delivery vehicles comprising *Pseudomonas* exotoxin are administered in doses in which the proportion by weight of *Pseudomonas* exotoxin is about 0.01 to about 100 μg of the total weight of the loaded delivery vehicle-exotoxin administered. In some preferred embodiments, delivery vehicles comprising *Pseudomonas* exotoxin are administered in doses in which the proportion by weight of *Pseudomonas* exotoxin is about 0.1 to about 10 μg of the total weight of the administered dose. In some preferred embodiments, delivery vehicles comprising *Pseudomonas* exotoxin are administered in doses in which the proportion by weight of *Pseudomonas* exotoxin is about 0.3 to about 2.2 μg of the total weight of the administered dose.

To dose delivery vehicles comprising radioisotopes in pharmaceutical compositions useful as imaging agents, it is presumed that each delivery vehicle is loaded with one radioactive active moiety. The amount of radioisotope to be administered is dependent upon the radioisotope. Those having ordinary skill in the art can readily formulate the amount of delivery vehicle-imaging agent to be administered based upon the specific activity and energy of a given radionuclide used as an active moiety. Typically about 0.1 to about 100 millicuries per dose of imaging agent, preferably about 1 to about 10 millicuries, most often about 2 to about 5 millicuries are administered.

Thus, pharmaceutical compositions that are useful imaging agents comprise delivery vehicles comprising a radioactive moiety in an amount ranging from about 0.1 to about 100 millicuries, in some embodiments preferably about 1 to about 10 millicuries, in some embodiments preferably about 2 to about 5 millicuries, in some embodiments more preferably about 1 to about 5 millicuries.

Examples of dosages include: $^{131}$I=between about 0.1 to about 100 millicuries per dose, in some embodiments preferably about 1 to about 10 millicuries, in some embodiments about 2 to about 5 millicuries, and in some embodiments about 4 millicuries; $^{111}$In=between about 0.1 to about 100 millicuries per dose, in some embodiments preferably about 1 to about 10 millicuries, in some embodiments about 1 to about 5 millicuries, and in some embodiments about 2 millicuries, $^{99m}$Tc=between about 0.1 to about 100 millicuries per dose, in some embodiments preferably about 5 to about 75 millicuries, in some embodiments about 10 to about 50 millicuries, and in some embodiments about 27 millicuries.

Depending upon the specific activity of the radioactive moiety and the weight of the delivery vehicle, the dosage defined by weight varies. For example, in a pharmaceutical composition comprising an $^{131}$I-loaded platelet in which the specific activity of $^{131}$I-loaded platelet is about 2000 Ci/mmol, administering the dose of about 0.1 to about 100 millicuries is the equivalent of 0.1 to about 100 μg $^{131}$I-loaded platelet, administering the dose of about 1 to about 10 millicuries is the equivalent of about 1 to about 10 μg of $^{131}$I-loaded platelet, administering the dose of about 2 to about 5 millicuries is equivalent to giving about 2 to about 5 μg of $^{131}$I-loaded platelet and administering the dose of about 1 to about 5 millicuries is equivalent to giving about 1 to about 5 μg of $^{131}$I-loaded platelet.

In a pharmaceutical composition comprising a loaded platelet comprising a single $^{111}$In in which the specific activity of $^{111}$In-loaded platelet is about 1 Ci/mmol, administering the dose of about 0.1 to about 100 millicuries is the equivalent of about 0.2 to about 200 mg $^{111}$In-loaded platelet, administering the dose of about 1 to about 10 millicuries is the equivalent of about 2 to about 20 mg of $^{111}$In-loaded platelet, administering the dose of about 2 to about 5 millicuries is equivalent to giving about 4 to about 10 mg of $^{111}$In-loaded platelet and administering the dose of about 1 to about 5 millicuries is equivalent to giving about 2 to about 10 mg of $^{111}$In-loaded platelet.

To load delivery vehicles with radioisotopes in pharmaceutical compositions useful as therapeutic agents, it is presumed that each delivery vehicle is loaded with one radioactive active moiety. The amount of radioisotope to be administered is dependent upon the radioisotope. Those having ordinary skill in the art can readily formulate the amount of delivery vehicle-radio-therapeutic agent to be administered based upon the specific activity and energy of a given radionuclide used as an active moiety. For therapeutics that comprise 131I, between about 10 to about 1000 nanomoles (nM), preferably about 50 to about 500 nM, more preferably about 300 nM of 131I at the tumor, per gram of tumor, is desirable. Thus, if there is about 1 gram of tumor, and about 0.1% of the administered dose is delivered to the tumor, about 0.5 to about 100 mg of 131I-delivery vehicle is administered. In some embodiments, about 1 to about 50 mg of 131I-delivery vehicle is administered. In some embodiments, about 5 to about 10 mg of $^{131}$I-delivery vehicle is administered. Wessels B. W. and R. D. Rogus (1984) Med. Phys. 11:638 and Kwok, C. S. et al. (1985) Med. Phys. 12:405, both of which are incorporated herein by reference, disclose detailed dose calculations for diagnostic and therapeutic vehicles which can be used in the preparation of pharmaceutical compositions of the present invention which include radioactive delivery vehicles.

E. Pharmaceutical Compositions

After a sufficiently purified delivery vehicle comprising active agent has been prepared, one will desire to prepare it into a pharmaceutical composition that can be administered in any suitable manner. Preferred administration techniques include parenteral administration, intravenous administration and infusion directly into a target tissue, such as a solid tumor or other neoplastic tissue. This is done by using for the last purification step a medium with a suitable pharmaceutical composition.

Suitable pharmaceutical compositions in accordance with the invention will generally comprise an amount of the desired delivery vehicle-active agent in accordance with the dosage information set forth above admixed with an acceptable pharmaceutical diluent or excipient, such as a sterile aqueous solution, to give an appropriate final concentration in accordance with the dosage information set forth above with respect to the active agent. Such formulations will typically include buffers such as phosphate buffered saline (PBS), or additional additives such as pharmaceutical excipients, stabilizing agents such as BSA or HSA, or salts such as sodium chloride.

For parenteral administration it is generally desirable to further render such compositions pharmaceutically acceptable by insuring their sterility, non-immunogenicity and non-pyrogenicity. Such techniques are generally well known in the art as exemplified by *Remington's Pharmaceutical Sciences,* 16th Ed. Mack Publishing Company (1980), incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

F. Therapeutic Methods

A therapeutic method is provided in accordance with the present invention. The method pertains to the delivery of an active agent to a target tissue in a vertebrate subject, and comprises: (a) exposing the target tissue to ionizing radiation; and (b) administering a delivery vehicle to the vertebrate subject before; after; during; before and after; before and during; during or after; or before, during and after exposing the target tissue to the ionizing radiation. Indeed, any combination of administering a delivery vehicle to the vertebrate subject before, during and/or after exposing the target tissue to the ionizing radiation falls within the scope of the present invention. The delivery vehicle comprises the therapeutic agent, and delivers the agent to the target tissue.

The target tissue is exposed to ionizing radiation in the amounts and ranges discussed herein. A preferred minimal dose of ionizing radiation comprises about 400 cGy. A more preferred dose comprises about 10 Gy, in that maximal platelet aggregation has been observed at this dosage level. Platelet aggregates are typically first observed in the target tissue one hour after irradiation and maximal platelet aggregation in target tissue is typically observed at about 24 hours after irradiation. After about 48 hours after irradiation, platelet aggregates begin to diminish.

In a preferred schedule of administration, delivery vehicles comprising the active agent are administered about one hour prior to irradiation or about ten minutes after irradiation. Applicant has observed that radiation induced platelet aggregation increased three-fold over untreated controls when delivery vehicles were administered about ten minutes after administration. When delivery vehicles were administered prior to irradiation, a ten-fold increase in platelet aggregation in tumors as compared to untreated controls was observed.

Optionally, delivery vehicles comprising the active agent are administered both about one hour prior to irradiation and about ten minutes after irradiation. Of course, dosage levels of the active agent are adjusted to reflect two administrations of the delivery vehicles comprising the active agent.

In a preferred embodiment of a therapeutic method of the present invention, the target tissue comprises a neoplasm. As described hereinabove, any neoplasm can be selectively targeted for delivery of a therapeutic agent in accordance with the method of the present invention.

Warm-blooded vertebrates comprise preferred subjects for treatment in accordance with the methods of the present invention. Therefore, the invention concerns mammals and birds.

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

A suitable therapeutic agent comprises any agent having a therapeutic effect, including but not limited to chemotherapeutics, toxins, radiotherapeutics, or radiosensitizing agents. Particular chemotherapeutics, toxins, radiotherapeutics, or radiosensitizing agents are set forth in detail above. Preferably, the therapeutic agent is administered in a pharmaceutically acceptable form comprising an effective amount of the desired therapeutic agent-delivery vehicle, as provided in accordance with the dosage information set forth above.

When the therapeutic agent is a radiosensitizing agent the method further comprises the step of again exposing the target tissue to ionizing radiation after delivery of the radiosensitizing agent-loaded delivery vehicles to the target tissue. Preferably, the target tissue is exposed to ionizing radiation at a time point of about 6 hours after the initial irradiation of the target tissue.

By way of further explanation, pharmacokinetic and pharmacodynamic studies were performed by studying the time course of radiolabeled delivery vehicles in various tissues, including tumor, liver, spleen and heart. Each region of interest was studied by measuring counts per pixel in each of the regions. Using $^{111}$In as a label, the time point for maximal localization in tumors was about 6 hours after initial tissue irradiation in accordance with the present invention. At about 24 hours after initial irradiation, increased platelet aggregation in tumors was observed; but, a concurrent increase in the platelet aggregation in liver, spleen and heart was observed. As would be apparent to one of ordinary skill in the art, the elucidation of these pharmacodynamic parameters facilitates the timing of a second dose of ionizing radiation to the target tissue, after a radiosensitizing agent has been delivered to the target tissue, so that desired therapeutic effects in the target tissue are maximized and undesired negative effects in other tissues are minimized.

G. Treatment of Angiogenesis

Angiogenesis, or the growth of new blood vessels, is an essential component to the growth of tumors (Folkman, J., N Engl J Med 28;333(26), 1757–1763 (1995)). These newly proliferating blood vessels have distinct expression of cell adhesion molecules (Wu et al., British Journal of Cancer68, 883–9 (1994)). P-selectin is one of many cell adhesion molecules expressed on the endothelium of angiogenic blood vessels (Brooks, P. C., Cancer Metastasis Rev. 15:187–194 (1996)).

In view of the relationship between P-selectin expression and platelet aggregation disclosed herein, a therapeutic method pertaining to the inhibition of angiogenesis is provided in accordance with the present invention. The present invention thus provides for a method for the inhibition of angiogenesis in a tissue, and thereby modulating events in the tissue which depend upon angiogenesis. Such a method particularly involves the exposure of a target tissue undergoing angiogenesis to ionizing radiation in conjunction with the administration of a delivery vehicle comprising a therapeutic agent, whereby the delivery vehicle is selectively delivered to the blood vessels and angiogenesis in the blood vessels is inhibited. Indeed, angiogenic blood vessels are provided "target tissues", as the term is used herein. Any therapeutic agent as characterized herein and/or that has an inhibitory effect on angiogenesis can be used in the method. Such agents can be referred to as "antiangiogenic agents". Representative therapeutic agents include coagulants and radiotherapeutics, as are more fully described herein above.

Angiogenesis includes a variety of processes involving neovascularization of a tissue including "sprouting", vasculogenesis, or vessel enlargement. With the exception of traumatic wound healing, corpus luteum formation and embryogenesis, it is believed that the majority of angiogenesis processes are associated with disease processes.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, capillary proliferation in atherosclerotic plaques and osteoporosis, and cancer associated disorders, such as solid tumors, solid tumor metastases, angiofibromas, retrolental fibroplasia, hemangiomas, Karposi's sarcoma and the like cancers which require neovascularization to support tumor growth.

Thus, methods which inhibit angiogenesis in a diseased tissue ameliorates symptoms of the disease and, depending upon the disease, can contribute to cure of the disease. In one embodiment, the invention contemplates inhibition of angiogenesis, per se, in a tissue. The extent of angiogenesis in a tissue, and therefore the extent of inhibition achieved by the present methods, can be evaluated by a variety of methods, such as the chick chorioallantoic membrane assay. The chick chorioallantoic membrane assay has be described in detail by others, and further has been used to measure both angiogenesis and neovascularization of tumor tissues. See Ausprunk et al., Am. J. Pathol., 79:597–618 (1975); Ossonski et al., *Cancer Res.*, 40:2300–2309 (1980); and U.S. Pat. No. 5,753,230, the entire contents of each of which herein incorporated by reference.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

Thus, in one related embodiment, a tissue to be treated is an inflamed tissue and the angiogenesis to be inhibited is inflamed tissue angiogenesis where there is neovascularization of inflamed tissue. In this case the method contemplates inhibition of angiogenesis in arthritic tissues, such as in a patient with chronic articular rheumatism, in immune or non-immune inflamed tissues, in psoriatic tissue and the like.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a hemangioma or angiofibroma and the like cancer, and the angiogenesis to be inhibited is tumor tissue angiogenesis where there is neovascularization of a tumor tissue.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor. Stated differently, the present invention provides for a method of modulating tumor neovascularization by modulating tumor angiogenesis according to the present methods. Similarly, the invention provides a method of modulating tumor growth by practicing the angiogenesis-modulating methods.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

H. Imaging Techniques

A diagnostic imaging method is provided in accordance with the present invention. The method pertains to the delivery of an imaging agent to a target tissue in a vertebrate subject, and comprises: (a) exposing the target tissue to ionizing radiation; (b) administering a delivery vehicle to the vertebrate subject before, after, during, or combinations thereof, exposing the target tissue to the ionizing radiation; and (c) detecting the imaging agent in the target tissue. The delivery vehicle comprises an imaging agent, and aggregates in the target tissue to thereby deliver the agent to the target tissue so that the imaging agent can be detected.

In a preferred embodiment of a diagnostic imaging method of the present invention, the target tissue comprises a neoplasm. As described hereinabove, any neoplasm can be selectively targeted for delivery of an imaging agent in accordance with the method of the present invention.

According to the imaging method of present invention, imaging agents are useful in diagnostic procedures as well as in procedures used to identify the location of cells of a target tissue, such as metastasized neoplastic cells. Imaging can be performed by many procedures well-known to those having ordinary skill in the art and the appropriate imaging agent useful in such procedures and as are described in detail herein above can be loaded in delivery vehicles as also described in detail herein. Imaging can be performed, for example, by radioscintigraphy, nuclear magnetic resonance imaging (MRI) or computed tomography (CT scan). The most commonly employed radionuclide imaging agents include radioactive iodine and indium.

Imaging by CT scan can employ a heavy metal such as iron chelates. MRI scanning can employ chelates of gadolinium or manganese. Additionally, positron emission tomography (PET) can be possible using positron emitters of oxygen, nitrogen, iron, carbon, or gallium.

EXAMPLES

The following Laboratory Examples have been included to illustrate preferred modes of the invention. Certain aspects of the following Laboratory Examples are described in terms of techniques and procedures found or contemplated by the present inventor to work well in the practice of the invention. These Laboratory Examples are exemplified through the use of standard laboratory practices of the inventor. In light of the present disclosure and the general level of skill in the art, those of skill will appreciate that the following Laboratory Examples are intended to be exemplary only and that numerous changes, modifications and alterations can be employed without departing from the spirit and scope of the invention.

Example 1

P-Selectin Accumulation in the Lumen of Irradiated Blood Vessels

Ionizing radiation induces the inflammatory response in part through leukocyte binding to cell adhesion molecules that are expressed on the vascular endothelium. The effects of x-irradiation on the pattern of immunohistochemical staining of CD62P(P-selectin) was studied. P-selectin was localized within cytoplasmic granules in the untreated vascular endothelium. P-selectin immunohistochemical staining was observed at the luminal surface of vascular endothelium within one hour of irradiation. Increased P-selectin staining at the blood tissue interface occurred primarily in pulmonary and intestinal blood vessels.

To determine whether P-selectin localization at the vascular lumen occurs through exocytosis of endothelial cells stores in addition to platelet aggregation, the vascular endothelium from the circulation were removed and endothelial cells were irradiated in vitro. The mechanisms by which ionizing radiation induced translocation of P-selectin were studied by using immuno-fluorescence of human umbilical vein endothelial cells (HUVEC) and confocal microscopy. Prior to irradiation, P-selectin is localized in cytoplasmic reservoirs of HUVEC. Following irradiation of HUVEC, P-selectin was translocated to the cell membrane, where it remained tethered. The threshold dose required for translocation of P-selectin to the cell membrane was 2 Gy.

To determine whether P-selectin in Weibel-Palade bodies requires microtubule-dependent membrane transport, microtubule depolymerizing agents, colcemid and nocodozol, were added. Microtubule-depolymerizing agents prevented radiation-induced P-selectin transocation to the cell membrane. Thus, P-selectin accumulates in irradiated blood vessels through both platelet aggregation and microtubule dependent exocytosis of storage reservoirs within the vascular endothelium.

Materials and Methods

Cell lines. Human umbilical vein endothelial cell (HUVEC) cultures were prepared from fresh (<24-hour-old) human umbilical veins transported to the laboratory in sterile buffer at 4° C. as described by Hallahan et al., *Biochemical & Biophysical Research Communications* 217: 784–795 (1995) and by Hallahan et al., *Cancer Research* 56:5150–5155 (1996). The vein was cannulated, filled with 0.2% collagenase, and incubated at 37° C. for 15 minutes. Cells were flushed and complete medium was added, followed by centrifugation at 2000 rpm for 5 min. The cell pellet was resuspended and maintained in M199 with 10% fetal calf serum, 10% human serum, and pen/strep/amphotericin B solution (Sigma) on gelatin-coated (0.2%) tissue culture dishes at 37° C. in 5% $CO_2$. The purity of endothelial cell cultures was verified by staining for factor VIII. Confluent cells were harvested with 0.1% collagenase 0.01% EDTA and subcultured at a ratio of 1:3. HUVECs were used at third passage; this reduced the number of passenger cells and allowed for uniform expression of cellular adhesion molecules. Thrombin was purchased from Sigma.

Immunofluorescence microscopy of P-selectin in endothelial cells. Primary-culture vascular endothelial cells were grown to 80% confluence on glass slides. During inhibition experiments, HUVEC were incubated with colcemid (500 nM) or nocodozol (500 nM) for 20 minutes prior to irradiation. Cytochalazin-B (1 mM) was added for 60 minutes before irradiation. Cells were treated with either thrombin or gamma irradiation from a $^{60}Co$ source (GAMMACELL™ 220) as described by Hallahan, D. E. et al., *Biochemical & Biophysical Research Communications* 217:784–795 (1995) and by Hallahan, D. E. et al., *Cancer Research* 56:5150–5155 (1996). After treatment, HUVEC were fixed with 4% paraformaldehyde for 10 min at room temperature, washed 3 times with antibody buffer (4 gm bovine serum albumin, 0.1 gm sodium azide, 0.75 gm glycine, and 100 µl PBS) and 2 times in Hanks salt solution. Non-specific binding of antibody was blocked with 50% goat serum for 30 min at 37° C. in a humid chamber.

Cells were then washed with antibody buffer and Hanks salt solution and incubated with 100 µl of 10 µg/mL anti-P-selectin primary antibody (Pharmingen, catalog #09361A, rabbit anti-human) for 2 to 3 hours at 37° C. in a humid chamber. Cells were then washed with antibody buffers and Hanks solution and incubated with 10 µl of a 1:300 dilution of FITC conjugated goat anti-rabbit IgG (cat. #L42001) for 30 min. Cells were washed, counterstained with DAPI, and mounted with anti-fade mounting medium. After washings, cells were visualized with a Zeiss Photomicroscope III fluorescence microscope for incident-light excitation. Slides were mounted and examined for fluorescence and by phase microscopy.

Using images of cells from a 100× objective using confocal microscopy, fluorescence intensity was measured, in pixels, on the cell membrane. Fluorescence intensity was measured by NIH Image software as described by Hallahan, D. E. and Virudachalam, S., *Proc. Natl. Acad. Sci. USA* 94:6432–7 (1997). Ten randomly selected cells were imaged. Experiments were performed 3 to 4 times. All data were analyzed by use of CHI SQUARE STATISTICA™ for WINDOWS®) software (StatSoft, Inc., Tulsa, Okla.).

Irradiation of mice. C57BL6 Mice (Jackson Laboratories) were irradiated as described by Hallahan, D. E. and Virudachalam, S., *Cancer Research* 57, 2096–2099 (1997) and by Hallahan, D. E. and Virudachalam, S., *Proc. Natl. Acad. Sci. USA* 94:6432–7 (1997). Briefly, mice were immobilized in a lucite tube. Lead was shaped over the abdomen during thoracic irradiation and over the thorax during abdominal irradiation. The chest or abdomen were irradiated with 10 Gy at the rate of 2 Gy per minute losing 150 kv x-rays from a General Electric MAXITRON™ generator. Ten, 30, 60, or 120 minutes after irradiation, mice were euthanized by intraperitoneal injection of xylazine and ketamine. Tissues were fixed in formalin and embedded in paraffin. Tissue blocks were then sectioned in 5 µm thick sections.

Immunohistochemistry. Tissue sections were baked at 60° C. for 1 hour, cleared in xylene, and hydrated through a descending alcohol series to distilled water. For P-selectin and CD45 immunostaining, the hydrated sections were incubated with Protease I (Ventana Biotech, Tucson, Ariz.) for 8 minutes at 42° C. For ICAM immunostaining, the hydrated sections were incubated with Protease II (Ventana Biotech) for 8 minutes at 42° C. After brief washing in $ddH_2O$, endogenous activity was blocked by treatment of the sections with 3% hydrogen peroxide in methanol for 20 min. Two tissue sections from each mouse were then incubated overnight at 4° C. at a titer of 2.5 µg/mL for anti-P-selectin antibody (Pharmingen, San Diego, Calif.). One slide from each sample was treated in a similar fashion and incubated overnight in normal serum immunoglobulin (Ventana Medical Systems, Tucson, Ariz.).

The immunohistochemical staining was performed on a Ventana GEN11™ system (Ventana Medical Systems). The Ventana GEN11™ system uses an indirect strepavidin-biotin system conjugated with horseradish peroxidase for detection of the immunocomplex and diaminobenzidine as a substrate for localization. The Ventana GEN11™ system uses a cartridge delivered avidin/biotin blocking kit to block endogenous biotin. The immunostained sections were counterstained with hematoxylin, dehydrated through an ascending alcohol series, cleared, and coverslipped. Tissue sections were imaged using 40× objective lens.

Results

Localization of P-selectin to the blood-tissue interface in irradiated blood vessels. To determine whether ionizing radiation altered the immunostaining pattern of P-selectin, C57BL6 mice were treated with thoracic irradiation (10 Gy). During immunohistochemical analysis of the irradiated tissues, it was observed that P-selectin protein in the vascular endothelium was localized to the tissue-blood interface at one hour after irradiation. Prior to irradiation, P-selectin staining was localized to the endothelial cells, but it was redistributed to the tissue-blood interface within 1 hour of irradiation. Leukocytes localized with redistributed P-selectin at the blood-tissue interface in irradiated pulmonary vessels.

To determine whether P-selectin redistribution to the vascular lumen after irradiation is specific to the lung, tissue sections from irradiated small intestine and colon were studied. The irradiated small intestine showed P-selectin localized to the blood-tissue interface at one hour after irradiation. Likewise, the vascular endothelium within the irradiated large intestine showed P-selectin localized to the vascular lumen.

To study the duration of P-selectin translocation to the luminal surface of irradiated blood vessels, later time points were studied. P-selectin localization to the blood-tissue interface persisted at 6 hours after irradiation. P-selectin is also present in the granules of platelets and was therefore observed within platelet aggregates that were first observed within irradiated blood vessels at 6 hours after irradiation. At 24 hours, P-selectin immunohistochemistry revealed staining of platelet aggregates within irradiated blood vessels of the lung. Platelet aggregation was transient, and resolution began by 48 hours after irradiation. At 24 hours after irradiation, leukocytes adhered to P-selectin within platelet aggregates.

Radiation-induced P-selectin exocytosis in irradiated endothelial cells. To determine whether radiation-induced P-selectin accumulation in the vascular lumen was specific for vascular endothelium in vivo, primary-culture HUVEC were irradiated. The in vitro endothelial cell model provides a means to study direct effects of ionizing radiation on the vascular endothelium by removing platelets, leukocytes and thrombin. Immunofluorescence microscopy allowed the visualization of P-selectin in endothelial cells.

P-selectin was compartmentalized in Weibel-Palade bodies, which underwent membrane transport to the cell membrane after exposure to ionizing radiation. Prior to irradiation, P-selectin was localized to storage reservoirs within the cytoplasm of endothelial cells. At 15 minutes after irradiation (2 Gy), WPB began translocation to the cell apical membrane. Translocation of P-selectin to the cell membrane was complete at 30 min after irradiation. P-selectin remained tethered to the cell membranes at 60 minutes after exposure to 2 Gy and P-selectin immunofluorescence stained in a starry sky pattern. The increased intensity of immunofluorescence after exocytosis can be due to increased accessibility of epitopes once P-selectin is translocated to the cell membrane. P-selectin ELISA analysis of medium showed no release of P-selectin into the medium at 1, 2, 4, 6 or 24 hours after irradiation.

To determine whether radiation-induced P-selectin translocation is dose-dependent, HUVEC were treated with 1, 2 and 5 Gy. Confocal microscopy was used to measure immunofluorescence on the cell surface, which was quantified by NIH Image software. There was minimal WPB exocytosis in response to 1 Gy, but it was observed that 2 Gy was sufficient to induce P-selectin translocation to the cell membrane of endothelial cells. Higher doses induced no more rapid or efficient translocation than 2 Gy, indicating that there is minimal dose dependence in x-ray-induced P-selectin translocation.

P-selectin immunofluorescence of endothelial cells treated with microtubule depolymerizing agents. Membrane transport of storage reservoirs requires motor protein tracking over the cytoskeleton, as described by Eyden, B. P., *Journal of Submicroscopic Cytology & Pathology* 25:145–8 (1993) and by Sinha, S. and Wagner, D. D., *European Journal of Cell Biology* 43:377–83 (1987). To determine whether microtubules or actin are required for radiation-induced exocytosis of P-selectin, the microtubule depolymerizing agents, colcemid and nocodozol, or the actin antagonist cytochalasin-B were utilized. HUVEC were pretreated with these agents for 40 min followed by irradiation. Immunofluorescent confocal microscopy showed P-selectin translocation to the cell membrane of irradiated HUVEC. At 60 min following irradiation, HUVEC treated with radiation alone showed the starry sky pattern of immuno-fluorescence of P-selectin on the cell membrane.

The microtubule depolymerizing agents colcemid and nocodozol inhibited x-ray induced translocation of P-selectin and showed P-selectin localized to cytoplasmic storage reservoirs in a pattern similar to untreated control. Conversely, cells pretreated with cytochalasin-B showed no inhibition of P-selectin translocation. Localization of P-selectin on the cell membrane was quantified by use of immunofluorescence confocal microscopy, which was quantified by NIH Image software. This showed an 8-fold increase in P-selectin immunofluorescence on the cell surface, which was abrogated by Colcemid and nocodozol, but not the actin antagonist cytochalasin-B.

Example 2

Absence of P-Selectin Immunostaining in the Vascular Endothelium is Associated with the Attenuation of Radiation-Induced Platelet Aggregation P-selectin is an adhesion molecule sequestered in storage reservoirs in platelets and vascular endothelium and rapidly undergoes exocytosis following x-irradiation. P-selectin adheres to sialylated molecules on the surface of leukocytes to slow the flow of the cells and begin leukocyte activation. To determine whether a P-selectin contributes to the radiation response, the immunohistochemical pattern of staining of P-selectin in irradiated tissues was studied. Prior to x-irradiation, P-selectin is present within the vascular endothelium. Within one to two hours, P-selectin stains along the blood-tissue interface. At four to six hours after irradiation, P-selectin staining filled the vascular lumen in a pattern consistent with platelet aggregation.

To verify that platelet aggregation was present in these irradiated blood vessels, tissue sections underwent immunohistochemical staining with anti-GPIIIa antibodies that stained platelets. No P-selectin or GPIIIa staining was found in the brain or kidney, but both P-selectin and GPIIIa staining were present in the irradiated lung, intestine and tumor vessels. The P-selectin knockout mouse was used to study platelet aggregation (i.e. GPIIIa accumulation) in the absence of P-selectin staining in the vascular endothelium. The GPIIIa staining was not localized to the lumen of irradiated blood vessels in the knockout mouse, but extravasated into the irradiated lung, and tumors. Knockout of the P-selectin gene leads to extravasation of blood components to the irradiated tissues.

Materials And Methods

Irradiation of Mice. P-selectin knockout mice, prepared as described by Canadas et al. *Cell* 74:541–54 (1993), were obtained from Jackson Laboratories. Mice were bred in the transgenic mouse core laboratory at Vanderbilt University, Nashville, Tenn. Five- to six-week-old mice were irradiated as described by Hallahan, D. E. and Virudachalam, S., *Cancer Research* 57:2096–2099 (1997) and by Hallahan, D. E. and Virudachalam, S., *Proc. Natl. Acad. Sci. USA* 94:6432–7 (1997). Briefly, mice were immobilized in lucite cylinders. Lead shielding was used to eliminate dose to the abdomen during thoracic irradiation. Likewise, thoracic shielding was used during abdominal irradiation. Mice were treated with 250 KV x-rays using a General Electric MAX-ITRON™ generator at a dose rate of 2 Gy per minute. After irradiation, mice were euthanized by intraperitoneal injection of xylazine and ketamine. Tissues were excised and analyzed for platelet aggregation at 6, 24 and 48 hours after irradiation. Tissues were fixed in formalin and embedded in paraffin.

Immunohistochemistry of Tissue Sections. Tissue sections were baked at 60° C. for 1 hour, cleared in xylene, and hydrated through a descending alcohol series to distilled water. After brief washing in distilled H$_2$O, endogenous activity was blocked by treatment of the sections with 3% hydrogen peroxide in methanol for 20 minutes. Two tissue sections from each mouse were then incubated overnight at 4° C. at a titer of 2.5 µg/mL for anti-P-selectin antibody (Pharmingen, San Diego, Calif.) or platelet antibody anti-GP-IIIa (Pharmingen, San Diego, Calif.). Increased GP-IIIa staining as compared to untreated controls determined the presence of platelet aggregation. One section from each lung was treated in a similar fashion and incubated overnight in normal serum immunoglobulin (Ventana Medical Systems, Tucson, Ariz.). The immunohistochemical staining was performed on a Ventana GEN11™ system (Ventana Medical Systems) which uses an indirect strepavidin-biotin system conjugated with horseradish peroxidase for detecting the immunocomplex and diaminobenzidine as a substrate for localization, as well as a cartridge delivered avidin/biotin blocking kit to block endogenous biotin. The immunostained sections were counterstained with eosin and hematoxylin, dehydrated through an ascending alcohol series, cleared, and coverslipped.

Immunofluorescence Staining of platelet aggregates in irradiated blood vessels. Immunofluorescence staining was performed as described by Hallahan, D. E. and Virudachalam, S., Cancer Research 57:2096–2099 (1997) and by Hallahan, D. E. and Virudachalam, S., Proc. Natl. Acad. Sci. USA 94:6432–7 (1997). Tissue sections (5 µm) were mounted on slides and labeled with anti-GP-IIIa antibodies as described above. After incubation with biotinylated secondary antibody, sections were incubated with 200 µl of Avidin-Cy3 (10 µg/mL) for 30 min in a humid chamber at room temperature. Avidin-Cy3 (Amersham), 5 µg/mL was added to 200 µL of blocking buffer and filtered through a 0.2 µm Millipore filter, before addition of the fluorochrome to slides. Coverslips were removed, and sections were washed with 4× SSC/0.1% solution of a detergent sold under the registered trademark TRITON®X by Rohm and Hass Company of Philadelphia, Pa. at room temperature. Slides were counterstained in DAPI and rinsed with 2× SSC for 10 seconds. Coverslips were then placed on slides with antifade and blotted. Immunofluorescent images were visualized with a Zeiss Photomicroscope III fluorescence microscope.

Platelet aggregation was quantified by measuring fluorescence intensity in blood vessels of tissue stained with anti-GPIIIa antibody (Pharmingen, San Diego, Calif.). Blood vessels were identified by auto-fluorescence of red blood cells using green filter. The filter was then changed to red wavelengths so that Cy3 stained platelets could be quantified. Fluorescence intensity within blood vessels measured using 40× objective microscopic images of tissues sections. Ten blood vessels in each tissue section were photographed using CCD camera. Fluorescence intensity was measured by NIH Image software as described by Hallahan, D. E. and Virudachalam, S., Cancer Research 57:2096–2099 (1997) and by Hallahan, D. E. and Virudachalam, S., Proc. Natl. Acad. Sci. USA 94:6432–7 (1997). Platelet aggregates were defined as the presence of increased GP-IIIa staining in blood vessels. The percentage of blood vessels with GP-IIIa staining was determined in 4 mice, each treated with x-rays or sham irradiation. A total of 10 vessels in each of 4 mice (40 vessels) were measured. All data were analyzed by use of Students Paired T-test.

Tumor implantation in rodents: GL-261 glioma cells were maintained in F-12/DME 50% mixture and 7% fetal calf serum, and penicillin and streptomycin. Subconfluent tumor cells were trypsinized, washed, and injected subcutaneously into the hindlimb of C57BL6 mice (Jackson Labs). Tumors were grown to 400 mm$^3$. Tumors were treated with x-irradiation using 250 kV x-rays as described by Hallahan, D. E. et al., Nature Medicine 1:786–791 (1995). Tumors were treated with 10 Gy at a dose rate of 1 Gy per minute.

P-selectin −/− mice were obtained from Jackson Laboratories (Bar Harbor, Me.). GL261 cells (106) were injected subcutaneously into the hindlimb of P-selectin −/− mice. Tumors were growth to a volume of 400 mm$^3$ and irradiated with 10 Gy. At 6 and 24 hours following irradiation, mice were euthanized by intraperitoneal injection of xylazine and ketamine. Tumors were fixed in formalin and embedded in paraffin. Tumors were sectioned and stained with the anti-GPIIIa antibody as described above.

Results

Histologic Pattern of P-selectin Expression in Irradiated Tissues. To determine whether platelet aggregation in irradiated blood vessels was associated with WPB exocytosis, immunohistochemical analysis of P-selectin, one of the WPB components was utilized. C57BL6 mice were treated with thoracic irradiation and tissues were fixed at the indicated times. Prior to irradiation, P-selectin was localized to the vascular endothelium. Within 60 minutes of irradiation, P-selectin was localized to the blood-tissue interface. P-selectin staining extended into the vascular lumen. At 4 hours after irradiation, P-selectin in platelet aggregates was stained within these blood vessels. Platelet aggregation continued to accumulate in irradiated blood vessels over 24 hours.

Association of radiation-induced platelet aggregation with P-selectin staining To differentiate between P-selectin in platelets and P-selectin in the endothelium, an anti-GPIIIa antibody to platelets was utilized. GPIIIa staining showed no platelet aggregation at one hour, indicating that x-ray induced intraluminal P-selectin can be of endothelial origin at this early time point. To quantify platelet aggregation, tissue sections from irradiated lungs with anti-GPIIIa antibody were stained. The percentage of irradiated blood vessels with platelet aggregates increased over time. Four hours after irradiation, 40% of blood vessels showed platelet aggregation. The percentage of pulmonary vessels with aggregates increased to 75% at 24 hours (p=0.01). Thereafter, platelet aggregation decreases.

Platelet aggregation is attenuated by antibodies to P-selectin and is markedly delayed in P-selectin −/− mice, as described by Subramaniam et al., Blood87:123842(1996) and by Boukerche, H., British Journal of Haematology 92:442–51 (1996). To determine whether P-selectin staining in the vascular endothelium is associated with platelet aggregation, the number of platelet aggregates in untreated murine blood vessels that stained positively for P-selectin were studied, as compared to tissues without P-selectin. P-selectin staining was found in large pulmonary blood vessels, but not in the pulmonary capillary endothelium. P-selectin staining was also observed in the irradiated small intestine endothelium. P-selectin staining was not observed in the irradiated brain or kidney.

To determine whether P-selectin staining was associated with radiation-induced platelet aggregation, platelets were quantified using anti-GPIIIa antibody and immunofluorescence. The brain, lung, kidney, small intestine and large intestine were each irradiated and tissues were excised at 24 h after irradiation. Platelet aggregation in irradiated blood vessels was quantified by GPIIIa immunothoracense. Tissues with no P-selectin staining showed an increase in GP-IIIa staining in 8% (brain) and 5% (kidney) as compared to tissues with P-selectin staining in the endothelium 75% (lung), 85% (small intestine) and 88% (large intestine) (p=0.002). Moreover, the pulmonary microvascular endothelium did not contain P-selectin and did not show platelet aggregation.

Absence of radiation induced platelet aggregation in blood vessels of P-selectin −/− mice. To determine whether P-selectin is required for radiation-induced platelet aggregation, P-selectin knockout mice were irradiated and stained for platelets utilizing the platelet antibody anti-GP IIIa. Marked attenuation of platelet aggregation in intestines of irradiated P-selectin knockout mice. Immunohistochemical staining for platelet antigens was utilized to measure of the difference in platelet aggregation in the P-selectin knockout mouse as compared to the P-selectin +/+ mouse. FACS analysis of platelets was performed by use of anti-GPIIIa antibody staining of washed blood components and showed no difference in GPIIIa platelet staining between wild-type and knockout mice. In tissue sections from control mice, there was no difference in the fluorescence pattern when wild-type mice as compared to the knockout mice. Increased platelet aggregation in blood vessels was observed at 6 hours following irradiation of wild-type mice. The percentage of blood vessels with platelet aggregation was abrogated in the P-selectin knockout mouse. Radiation-induced platelet aggregation was present in 10% of blood vessels as compared to 85% in wild type mice.

To determine whether x-ray-induced platelet aggregation is also attenuated in angiogenic blood vessels in P-selectin −/− mice, syngeneic tumors were induced in the hind lmibs of P-selectin +/+ mice and knockouts. GL261 gliomas were induced in P-selectin −/− and P-selectin +/+C57BL6 mice. Untreated control tumors showed no difference in baseline staining for GPIIIa. Following x-irradiation with 10 Gy, tumors were sectioned and stained for GP-IIIa. Irradiated tumors in P-selectin +/+ mice showed platelet aggregation at 6 h. Tumors in P-selectin −/− mice, however, showed no increase in GP-IIIa staining in blood vessels at 1, 4, 6 or 24 hours after irradiation as compared to untreated controls.

GPIIIa staining showed that platelets extravasated from irradiated blood vessels into irradiated tissues. Red blood cells also extravasated into irradiated tissues. Platelets and RBC's within the lungs of irradiated P-selectin −/− mice were also studied. P-selectin −/− mice treated with 10 Gy thoracic irradiation developed tachypnea and respiratory distress within seven days. In contrast, P-selectin +/+ mice showed no evidence of respiratory distress following 16 Gy thoracic irradiation. Histologic sections of lungs from P-selectin −/− mice at seven days following irradiation show hemorrhage into the alveoli. In contrast, P-selectin +/+ mice show no extravasation of blood components into the irradiated lung.

Example 3

X-ray-induced P-selectin Localization to the Lumen of Tumor Blood Vessels

P-selectin is a cell adhesion molecule that is sequestered in Weibel-Palade storage reservoirs within the vascular endothelium and a granules in platelets. P-selectin is rapidly translocated to the vascular lumen after tissue injury to initiate the adhesion and activation of platelets and leukocytes. In this Example, the histologic pattern of P-selectin expression in irradiated tumor blood vessels was studied. P-selectin was localized within the endothelium of tumor vessels prior to irradiation. At one to six hours following irradiation, P-selectin was mobilized to the lumen of blood vessels.

To determine whether radiation-induced vascular lumen localization of P-selectin was tumor type-specific or species-specific, tumors in rats, C3H mice, C57BL6 mice and nude mice were studied. P-selectin localization to the vascular lumen was present in all tumors and all species studied. Irradiated intracranial gliomas showed P-selectin localization to the vascular lumen within one hour, whereas blood vessels in normal brain showed no P-selectin staining in the endothelium and no localization to the irradiated vascular lumen. Radiation-induced P-selectin localization to the vascular lumen increased in time-dependent manner, until 24 hours after irradiation.

P-selectin in platelets can account for the time dependent increase in staining within the vascular lumen after irradiation. Immunohistochemistry for platelet antigen GP-IIIa was utilized to differentiate between endothelial and platelet localization of P-selectin. It was found that GP-IIIa staining was not present at one hour after irradiation, but increased at 6 hours and 24 hours. P-selectin localization to the vascular lumen at 6 to 24 hours was, in part, associated with platelet aggregation. These findings indicate that radiation-induced P-selectin staining in the vascular lumen of neoplasms is associated with aggregation of platelets. Radiation-induced localization of P-selectin to the vascular lumen is specific to the microvasculature of malignant gliomas and is not present in the blood vessels of the irradiated normal brain.

Methods

Maintenance of Tumor Cell Lines Tumors were induced by injection of tumor cells either subcutaneously or stereotactically into the rat brain. Rat C6 glioma cells were maintained in Ham's F10 medium with 15% horse serum, 2.5% fetal bovine serum, and 10 mM HEPES. Murine GL261 glioma cells were maintained in an F-12/DME 50% mixture and 7% fetal calf serum, and pen/strep. The human colon carcinoma cell line WIDR was maintained in MEMα, 1% NEAA and 10% fetal calf serum, and pen/strep.

Tumor induction in rodents Subconfluent tumor cells were trypsinized, washed, and injected subcutaneously into the hind limbs of mice. MCA4 tumors were excised, minced, and implanted by use of an 18-gauge needle sub-cutaneously into the hind limbs of C3H mice (Jackson Labs). Lewis lung carcinoma cells ($10^6$) were injected into the hind limbs of C57BL6 mice (Jackson Labs). Rat C6 cells were injected into Wistar rats (250–300 g) (Charles River, Wilmington, Mass.). Human colon carcinoma WIDR cells ($10^6$) were injected into nude mice (Jackson Labs). Tumors were grown to a volume of about 300 to about 500 mm³ prior to treatment with radiation or cytokines.

Treatment of tumors with x-irradiation. Tumors were treated with 250 kV x-rays as described by Hallahan, D. E. et al., *Nature Medicine* 1:786 (1995), with 2, 4, or 10 Gy at a dose rate of 1 Gy per minute. At 1, 6, and 24 hours after irradiation, mice were sacrificed by intraperitoneal injection of xylazine and ketamine.

Immunohistochemical staining for expression of cell adhesion molecules. Formalin fixed tumors were embedded in paraffin blocks and sectioned (5 μm thick). Sections were placed unto SUPERFROST PLUS™ glass slides (Fisher Scientific). Tissue sections were baked at 60° C. for 1 hour, cleared in xylene, and hydrated through a descending alcohol series to distilled water. After brief washing in ddH$_2$O, endogenous activity was blocked by treatment of the sections with 3% hydrogen peroxide in methanol for 20 min. Two tissue sections from each case were then incubated overnight at 4° C. at a concentration of 2.5 µg/mL for anti-P-selectin monoclonal (Pharmigen, San Diego, Calif.) and anti-GP-IIIa (Pharmigen, San Diego, Calif.) monoclonal antibodies. One slide from each sample was treated in a similar fashion and incubated overnight in normal serum immunoglobulin (Ventana Medical Systems, Tucson, Ariz.). The immunohistochemical staining was performed on a Ventana GEN11™ system (Ventana Medical Systems). The Ventana GEN11™ uses an indirect strepavidin-biotin system conjugated with horseradish peroxidase for detecting the immunocomplex and diaminobenzidine as a substrate for localization. The Ventana GEN11™ uses a cartridge delivered avidin/biotin blocking kit to block endogenous biotin. The immunostained sections were counterstained with hematoxylin, dehydrated through an ascending alcohol series, cleared, and coverslipped. Stained sections were imaged under a 40× objective. All blood vessels throughout the entire section were observed, and 3 to 5 sections were analyzed for each tumor.

Brain tumor model. intracranial gliomas were induced by stereotactic injection of rat C6 glioma cells into rat brains. Intracranial gliomas were allowed to grow for 14 days. C6 cells were maintained in Ham's F10 medium with 15% horse serum, 2.5% fetal bovine serum, and 10 mM HEPES. Growing cells were trypsinized and resuspended in PBS at $10^8$ cells/mL. Male Wistar rats (250–300 g) (Charles River, Wilmington, Mass.) were anaesthetized with a mixture of ketamine (90 mg/kg) and xylazine (10 mg/kg) and placed in a stereotactic frame (David Kopf Instruments, Tujunga, Calif.). The head was shaved and the skin incised, and a hole was drilled in the skull with a 1.8 mm trephine (Fine Science Tools Inc., Foster City, Calif.). Ten microliters of cell suspension were injected 4 mm beneath the surface of the skull with a 50 µl Hamilton syringe 2 mm from the midline and 2 mm anterior to the coronal suture. The skull was sealed with dental cement, the wound was stitched, and the animals were kept in separate cages for 2–3 days to prevent mutilation. Thirteen days after implantation, the animals were irradiated under anesthesia with 6 Gy (head only) in a $^{137}$Cs irradiator at 3.95 Gy/min. At 1, 6, 24, and 48 hours after irradiation, the animals were anesthetized again, and the brains were perfused with 10 mM sodium cacodylate, pH 7.0, 1.5% formaldehyde, 0.1% glutaraldehyde. The brains were further fixed in formaline, embedded in paraffin, and five micron sections processed as described.

Results

X-ray induced localization of P-selectin to the lumen of tumor vascular endothelium. P-selectin is constitutively expressed in the endothelium of pulmonary blood vessels (Hallahan, D. E. et al., *Cancer Research* 56: 5150 (1996)) and is sequestered in Weibel Palade bodies and in storage reservoirs in the endothelium. To determine whether P-selectin is present in the vascular endothelium of tumors, immunohistochemistry for P-selectin was utilized. Blood vessels from mouse breast carcinoma tumors MCA4, mouse lung carcinoma (Lewis lung carcinoma), and human colon carcinoma xenografts (WIDR) were studied. P-selectin was present in the vascular endothelium of each of these tumors. This finding was independent of the implantation site (brain, flank, or hind limb), strain of mouse (C3H, C57BL6, or nude), and species (mouse versus rat).

To determine whether radiation induces P-selectin localization to the endothelium and/or the vascular lumen of tumor blood vessels, tumors were treated with x-rays and immunohistochemical analysis was performed using anti-P-selectin antibody. Radiation-induced P-selectin mobilization to the vascular lumen was observed in all tumors including MCA4 in C3H mice, Lewis lung carcinoma in C57BL6 mice, and WIDR tumor xenografts in nude mice. P-selectin localization to the vascular lumen occurred in all tumor types, independent of the location of the tumor, strain of mouse, and species of rodent models.

Radiation-induced P-selectin localization to the vascular lumen in C6 brain tumors. The vascular endothelium in the brain is distinct from the endothelium in peripheral tissues (Barkalow, F. J. et al., *Blood* 88:4585 (1996)). Moreover, Weibel-Palade bodies have been identified in blood vessels within gliomas (Miyagami, M. and Nakamura, S., *Noshuyo Byori* 13:107 (1996)). To determine whether malignant gliomas induced in the brain have a distinct P-selectin expression as compared to that in peripheral tumors, C6 gliomas were induced in the brains of Wistar rats. The entire brain was irradiated with 6 Gy and sectioned at 1 and 6 hours after treatment. The normal brain blood vessels showed no P-selectin in untreated controls or following irradiation. On the other hand, gliomas showed P-selectin staining in the endothelium of untreated tumors. At 1 hour after irradiation, P-selectin staining at the blood-tissue interface increased. At 6 hours after irradiation, P-selectin staining in the lumen of blood vessels increased intensely.

X-ray induced P-selectin localization to the vascular lumen is dose-dependent. The vascular response to ionizing radiation is both dose- and time-dependent (Hallahan, D. E. et al., *Biochemical & Biophysical Research Communications* 217:784 (1995); Hallahan, D. E. et al., *Cancer Research* 56:5150 (1996); Hallahan, D. E. & Virudachalam, S., *Proc. Natl. Acad. Sci. USA* 94:6432 (1997)). To determine the threshold and plateau doses for induction of P-selectin localization to the vascular lumen, 1, 2, 4, 10 and 20 Gy doses were utilized. No localization of P-selectin to the vascular lumen in tumors treated with 1 Gy was observed. Efficient localization of P-selectin to the vascular lumen occurred following irradiation with 2 Gy. There was no increase in P-selectin localization to the vascular lumen or degree of staining at 1 hour, when higher doses of x-rays were used. This finding suggested that P-selectin localization to the vascular lumen occurs at least about at 1 hour with a threshold dose of about 2 Gy.

P-selectin staining increases in a time-dependent manner. Time-dependent P-selectin staining in irradiated tumor blood vessels was studied to determine whether P-selectin expression increased over 24 hours. Tumors treated with 2 and 10 Gy were compared. It was found that there was no increase in expression over 24 hours in tumors treated with 2 Gy. On the other hand, 10 Gy did produce an increase in P-selectin staining that accumulated over 24 hours. P-selectin staining was present at a low baseline level at 1 hour, and increased at 6 and 24 hours.

Platelet staining with anti-GP-IIIa. As noted above, GP-IIIa is a platelet antigen that is not found in the vascular endothelium. Anti-GP-IIIa antibodies were utilized to determine whether the time-dependent increase in P-selectin staining is due to platelet aggregation. Lewis lung carcinoma tumors in C57BL6 mice were irradiated and stained with anti-GP-IIIa antibody. Little GP-IIIa staining was found in blood vessels at 1 hour following irradiation. However, GP-IIIa staining increased at 6 and 24 hour following irradiation. These findings indicate that the increased P-selectin staining within the vascular lumen of irradiated tumors was due to platelet aggregation.

Example 4

Delivery of Platelet Vehicles to Irradiated Tissue in an Animal Subject

In accordance with the present invention, a non-invasive method of imaging platelet aggregation using indium-111 ($^{111}$In)—labeled platelet scan was performed in an animal model (mice) and was successful. Mice were exposed to lethal doses of 10.5 Gy whole body radiation. Renal uptake was shown within 2 hours of irradiation. For 4 subsequent days, the uptake of $^{111}$In platelets was significantly greater than in non-irradiated controls. This difference was amplified if the platelets were injected 3 days after irradiation and remained constant for the following 4 days.

Example 5

Delivery of Platelet Vehicles to Irradiated Tissue in a Human Subject

Indium-111 ($^{111}$In)-labeled platelet scintigraphy has been extensively used in the study of thrombosis and platelet kinetics in human subjects. There are two ligands that are widely used and these are oxine and tropolone. Both techniques preserve platelet function. In normal subjects, almost all of the radioisotope is bound to platelets. There is a significant reduction in radiolabeling efficiency and decreased percentage of $^{111}$In bound to platelets in vivo for patients with platelet counts <150,000/mL (Giannessi, D. et al., *Nucl. Med. Biol.* 22(3):399–403 (1996)).

As the two methods of labeling are quite comparable and oxine is commercially available and FDA approved for the study of platelets, $^{111}$In-oxine labeled platelets are utilized in this Example. The distribution of $^{111}$In-labeled platelets has been studied in normal volunteers, and $^{111}$In platelet imaging is a diagnostic protocol already in place at many medical facilities, including, for example, Vanderbilt Medical Center, Nashville, Tenn. Radioactivity in the lungs, heart, spleen, kidneys and testes have been determined for up to 75 hours after injection. After the first four hours, the activity in each of these organs, except liver and kidney, decreases at roughly the physical decay rate. The curves for the liver and kidney are flat and indicate continued accumulation of the radiotracer. The calculated mean radiation dose per unit administered activity is 0.6+/−0.07 rad/mCi for the total body and 34+/−6 rad/mCi for the spleen (Robertson, J. S. et al., *Radiology* 140(1):169–176 (1981)). The safety of $^{111}$In platelet scans in patients, including those with malignancies, has been well established (Oriuchi, N. et al., *European Journal of Nuclear Medicine* 25(3):247–252 (1998)).

Although planar images can give excellent information about the uptake especially in lesions of the extremities, or head and neck region, the presence of background uptake in overlying and underlying normal tissues such as the liver, spleen, and heart make the interpretation of intrathoracic and intraabdominal lesions more difficult. To get a better definition (i.e. improved contrast ratio) of three-dimensional (3D) uptake, SPECT functional imaging, in conjunction with CT or MRI images, is utilized. SPECT imaging with $^{111}$In labeled autologous platelets has been shown to provide increased image contrast and improved quantification over planar images (Suga, K. et al., *Clin Nucl Med* 8:595–601 (1996); Bacq, Z. M. et al., *Journal of Physiology* 273: 42P–43P (1977)).

Patients are stratified between intracranial and peripheral tumors at the time of registration. In patients, 42 mL of whole blood is collected, and platelets are separated and labeled with $^{111}$In oxine (Thakur ML 981) as described below. Patients are injected with 111 in oxine platelets preferably as soon as possible. (Anticipate approximately two hours following obtaining blood sample).

Patients are imaged 2–4 hours following injection of labeled platelets. Static images are obtained using a gamma camera fitted with a medium energy collimator peaked for 173–247 keV and 20% energy window. This is the Pre-RT scan to determine the baseline uptake in untreated tumors. Patients then begin radiation therapy. The dose per fraction, as well as the total dose, are determined by the treating radiation oncologist. 24–72 hours after injection of $_{111}$In oxine platelet, the patient is re-imaged. This is the Post-RT scan.

Radiation Therapy

Modality: External beam photon irradiation

Energy: 4–18 MV photon beams. Appropriate blocks, wedges, and bolus to deliver adequate dose to the planned target volume. Minimum source-axis distance of 80 cm.

Treatment Volume: All patients will receive local-regional irradiation. Fields are designed to encompass sites of disease requiring palliation or primary treatment. All fields must be treated each day.

Study, site, treatment intent and normal tissue considerations determine dose. Patients are stratified to either intracranial or peripheral tumors and Inverse dose escalation is conducted in these two groups independently. When stereotactic radiotherapy is used, the dose is prescribed to the tumor periphery.

Inverse ionizing radiation dose escalation of cohorts of 3*:

800–1200cGy/1 fraction
2000cGy/5 fractions
3000cGy/10 fractions
3500cGy/15 fractions
6000cGy/30 fractions

*Note: A failure to detect $^{111}$In is detected in tumors of three patients treated with 1000 cGy indicates that the alternative schema set forth herein below are to be followed. The observation of $^{111}$In uptake in tumors in 2 of 3 patients provides for the expansion of the cohort to a total of 6 patients. The observation of $^{111}$In uptake in tumors in 3 of 6 or 1 of 3 patients indicates that the dose is below threshold and the alternative schema set forth herein below are to be followed.

Dose Modifications And Management of Toxicity Dose modifications and management of toxicity secondary to radiation are left to the judgment of the treating radiation oncologist. No side effects are expected from the $^{111}$In oxine platelet scan.

Evaluation. Scans are evaluated degree of uptake on post-RT scans is compared to pre-RT scans on the same patient. The pharmacokinetics and pharmacodynamics of $^{111}$In uptake in tumors are determined by comparing scans obtained pre-RT to that obtained post-RT. If $^{111}$In is not visualized at a particular dose level, SPECT scanning is performed.

Alternative Schema. Visualization of $^{111}$In in fewer than 2 of 3 or 4 of 6 patients suggests that platelets might have been inactivated by $^{111}$In labeling. An alternative embodiment considers $^{99m}$Tc labeling and pretreatment of platelets with DDAVP (depoprovera). A greater number of fractions can be required to achieve platelet aggregation. Platelets can be given after the second and third fraction of irradiation. The pharmacokinetics can be too brief for gamma camera detection, and thus, scans should be performed at 1 to 6 hours after irradiation.

Platelets might be sequestered in spleen, etc. If so, the schedule of administration is changed to radiation followed immediately by radiolabeled-platelet administration.

Statistical Considerations. The observation of 111In uptake in tumors in 2 of 3 patients provides for the expansion of the cohort to a total of 6 patients. The observation of $^{111}$In uptake in tumors in 3 of 6 or 1 of 3 patients indicates that the dose is below threshold and the alternative schema described above are followed. In either case, quantification of gamma-ray detection is measured. Pharmacokinetics of $^{111}$In uptake is determined by comparing scans from day 1 to scans from day 2 at each dose level.

Drug Formulation, Availability, And Preparation. As would be appreciated by one of ordinary skill in the art, preparation, handling, and safe disposal of radioactive agents are performed in a self-contained, protective environment. Unused portions of radiolabeled platelets are discarded in appropriate labeled containers.

Drug Information.

| | |
|---|---|
| Drug name: | Indium-111 ($^{111}$In) |
| Availability: | Amersham |
| Storage and Stability: | Platelets are preferably administered immediately after labeling with $^{111}$In |
| Toxicity: | No anticipated toxicities. |
| Platelet labeling. | |

Preparation. 42 mL of whole blood collected in 8 mL of modified squibb ACD solution. Transfer to two 50 mL sterile propylpropylene tubes without the plunger or needle and very gently resuspend the blood with a pipette. Centrifuge 200 g maximum (900 RPM RC-3B) for 10 minutes. Separate platelet rich plasma (PRP), leaving 0.5–0.6 cm on the RBC layer and transfer to 12 mL sterile sarstedt conical tube. Centrifuge 1650 g maxim (2600 RPM) for 10 minutes. Transfer the platelet poor plasma (PPP) by pouring into sterile 12 mL tube. Suspend the platelet pellet in 4–5 mL of ACO saline and centrifuge for 5 minutes at 2600 RPM. Remove the supernatant and add 550–600 μCi $^{111}$In oxine with a sterile pipette to the platelet pellet. Mix with sterile pipette (5 gentle suctions up and down, do not introduce air bubbles. Incubate at room temperature for 20 minutes.

Centrifuge the $^{111}$In platelet tube at 1650 g maximum (2600 RPM) for 10 minutes. Save the supernatant. Determine supernatant activity using a dose calibrator. Resuspend In-platelets in 5 mL ACD/saline solution. Centrifuge 1650 g maximum (2600 RPM) for 8 minutes. Remove the supernatant and determine radioactivity of supernatant. Resuspend in 5 mL of ACD/saline. Centrifuge at 100 g maximum (500 RPM) for 5 minutes. Remove the supernatant and resuspend the $^{111}$In-platelets in 5 mL of PPP. Withdraw 5 mL of $^{111}$In platelets in a sterile syringe using a 19 gauge needle. Place an aliquot in a tube to send for CBC. Measure and document radioactivity.

Administration. The patient is injected with a 19 gauge needle and residual activity is measured. Labeling efficiency is determined and number of platelets used for labeling is calculated from CBC.

Example 6

X-Ray-Guided Drug Delivery by Radiation-Induced Aggregation of Electroporated Platelets This Example discloses the use of electroporation to prepare loaded platelets and contemplates reduced binding within the reticular endothelial system (RES) by platelets so prepared. In this Example, fluorochromes (Cy3, FITC) and gamma emitting radionuclides are loaded into platelets by use of electroporation. Additionally, small molecular weight compounds, which are inert in untreated tissues but demonstrate cytotoxicity in cells treated with ionizing radiation as disclosed herein, are also electroporated into platelets. Fluorescent markers (Cy3, FITC) are electroporated into platelets so that they can be identified by fluorescent microscopy.

Platelets are also loaded using the open channel system (OCS), receptor-mediated endocytosis using retention of liposomes, or reconstituted Sendai virus envelopes (RSVE). These techniques have been used to load chemotherapeutic agents such as adrimycin, cis-platinum and radioisotopes. Platelets are loaded by liposomes comprising chole steryl hexa decyesyl ether or chole steryl oleate. The liposome mediated platelet encapsulation is compared to electroporation using techniques described by Crawford, N., *Semin. Intervent. Cardiol.* 1:91–102 (1996). Platelets are also loaded with radiation sensitizing drugs in a similar manner for similar comparison. The loaded platelet delivery vehicles are then administered to a vertebrate subject and the target tissue is exposed to ionizing radiation via intersecting planes of irradiation in accordance with the methods of the present invention, including those set forth the foregoing Examples.

In separate experiments, platelets are loaded with $^{111}$In for studies of biodistribution and pharmacokinetics using gamma camera imaging and phospho imager plates to determine whole body biodistribution. Validation of Image Processing is performed by use of autoradiography and immunofluorescence of platelet antigen GP II/IIIa as described by Hallahan et al., *Cancer Research*, 58:5126–5220 (1998).

Improved biodistribution and pharmacokinetics are provided by optimizing the time interval, schedule and route of administration. Radiation sensitizing compounds such as the DNA PK inhibitor, R106 (ICOS, Inc., Borthwall, Wash.), ortyrosine kinase inhibitor, Su5416 (Sugen, Inc., and Fong et al., *Cancer Research* 59:99–106 (1999) and SU6668 (Sugen Inc., Redwood City, Calif.) are delivered, resulting in enhancement of subsequently delivered, intersecting planes of radiotherapy.

Examples 7–12

Delivery Vehicles for Use in X-ray Guided Drug Delivery

Examples 7–12 pertain to site-specific drug delivery systems that bind to irradiated tumor blood vessels. In Examples 7–12, radiation-inducible targets, including integrin $\beta_3$ (component of receptors GP-IIb/IIIa and $\alpha_v\beta_3$), for the delivery vehicles are described. The drug delivery methods and compositions of the present invention, including those described in Examples 7–12, are applicable to all vascularized neoplasms, thereby eliminating the problem of tumor-type specificity.

As disclosed herein above, ionizing radiation can be used to guide drugs to specific sites such as neoplasms or aberrant blood vessels. When blood vessels are treated with ionizing radiation, they respond by expressing a number of cell adhesion molecules and receptors that participate in homeostasis (referred to herein as "radiation inducible targets"). Mass spectrometry has been used to study protein expression within tumor blood vessels. A number of proteins have been characterized. One such protein is the integrin $\beta_3$. Other examples of radiation-induced molecules in blood vessels include ICAM-1, E-selectin and P-selectin.

Antibody binding to radiation inducible targets such as the cell adhesion molecules (CAMs) ICAM-1, E-selectin and P-selectin and the $\beta_3$ integrin is also disclosed herein. Ionizing radiation induces oxidative injury in the endothelium. The endothelium responds to maintain homeostasis by preserving the barrier function in blood vessels. This is accomplished by activation of inflammation and platelet aggregation. The mechanism by which radiation activates these homeostatic responses is, in part, through the induction of cell adhesion molecules. This requires the activation of the transcription factor NFκB, which regulates transcription of the ICAM-1 and E-selectin genes (Hallahan, 1995a; Hallahan, 1996b; Hallahan, 1998b). ICAM-1, E-selectin and P-selectin are induced by x-irradiation of the endothelium and bind to receptors on circulating leukocytes to initiate inflammation.

P-selectin (GMP140, CD62P) contributes to the inflammatory response following translocation from the cytoplasm of the vascular endothelium to the luminal surface of irradiated blood vessels. P-selectin is a cell adhesion molecule (CAM) that is sequestered in storage reservoirs within the vascular endothelium and granules in platelets. This CAM is translocated to the blood-tissue interface of the endothelium, and is not released from storage reservoirs, but remains tethered to the endothelial cell membrane (Johnston, 1989). P-selectin is rapidly translocated to the vascular lumen after tissue injury to initiate the adhesion and activation of platelets and leukocytes (Malik, 1996).

As disclosed herein, the histologic pattern of P-selectin expression in irradiated tumor blood vessels was studied and it was observed that P-selectin was localized within the endothelium of tumor vessels prior to treatment. At one hour following irradiation, P-selectin was localized to the lumen of blood vessels. P-selectin localization to the vascular lumen was present in all tumors and all species studied. Irradiated intracranial gliomas showed P-selectin localization to the vascular lumen within one hour, whereas blood vessels in normal brain showed no P-selectin staining in the endothelium and no localization to the irradiated vascular lumen.

An additional paradigm of radiation-induced targets for drug delivery is activation (conformational changes) of receptors within irradiated blood vessels. The integrin $\beta_3$ (component of receptor GPIIb/IIIa, $\alpha_{2b}\beta_3$) is activated and accumulates in the lumen of irradiated tumor blood vessels. Glycoproteins (GP) IIb and IIIa are members of the integrin superfamily and are the predominant surface glycoproteins in the platelet plasma membrane (Hawiger, 1992). These glycoproteins form a heterodimer GPIIb/IIIa (Carrell, 1985). Platelets contain several integrins, including the collagen receptor a2 μl, the fibronectin receptor $\alpha_5\beta_1$, and the vitronectin receptor $\alpha_v\beta_3$. Of these integrins, GPIIb-IIIa appears to be unique in that it is the only integrin that is restricted to platelets and cells of megakaryoblastic potential.

Human fibrinogen interacts with binding sites exposed on GPIIb-IIIa of stimulated platelets through the tentacles present on γ and α chains (Hawiger, 1982). The 12-residue carboxyl-terminal segment of the γ chain, encompassing residues 400–411, was pinpointed by Hawiger and others as the platelet receptor recognition domain. See e.g. Hawiger, (1992). Hawiger also showed that the sequence—RGD (a95–98) and (a572–575) are involved in the interaction of human fibrinogen α chain with receptors on activated platelets (Hawiger, 1989), but these regions are not essential for fibrinogen binding. Both domains contain the sequence RGD, identified previously as the cell recognition site of fibronectin. The presence of three domains on each half of the fibrinogen molecule, provides preferred conditions for tighter binding of fibrinogen to platelets and for their subsequent aggregation A fibrinogen molecule comprises three pairs of nonidentical chains arranged in an antiparallel configuration. The platelet receptor recognition domains encompass sequence 400–411 on the γ chain. RGD sequences 95–98 and 572–575 on the a chain bind, but are not essential. One fibrinogen molecule can be engaged in trans and cis interactions with platelet receptor GPIIb-IIIa.

Thus, applicant has identified several radiation-inducible target proteins in blood vessels. These include E-selectin, ICAM-1, P-selectin and the 3 integrin, which are expressed at radiation doses as low as 2 Gy. E-selectin and ICAM-1 are induced at the level of transcription in the vascular endothelium in response to ionizing radiation exposure. Levels of E-selectin protein and RNA induction following irradiation of vascular endothelial cells increase seven- to ten-fold. Likewise, levels of ICAM protein and RNA induction following irradiation of the endothelium increase approximately three-fold.

In addition to the transcriptional induction of genes in the vascular endothelium, preexisting proteins are translocated or activated following x-irradiation. For example, as disclosed herein, P-selectin is stored in a storage reservoir (Weibel Palade bodies), which undergo exocytosis in response to x-irradiation. P-selectin expression on the surface of endothelial cells in response to ionizing radiation has been observed. P-selectin accumulation within the lumen of tumor microvasculature following tumor irradiation was also observed. This response occurs at therapeutic doses of radiation (2 Gy) and typically occurs within one hour of x-irradiation.

$\beta_3$ also accumulates within the lumen of blood vessels in response to radiation. $\beta_3$ is associated with integrins $\alpha_v$ or $\alpha_{2b}$ to form heterodimers $\alpha_{2b}\beta_3$ and $\alpha_v\beta_3$. The heterodimer $\alpha_{2b}\beta_3$ is the component of a receptor on activated platelets, glycoprotein IIb/IIIa (GPIIb/IIIa), while $\alpha_v\beta_3$ is the vitronectin receptor. As disclosed herein, while several other radiation-induced molecules can be targeted within tumor blood vessels, the $\beta_3$ target for drug delivery is a preferred target for site-specific peptide binding within tumor blood vessels following irradiation.

As set forth in Examples 7–12, peptides and antibodies that bind to $\beta_3$ have been studied. $\beta_3$-binding proteins have been conjugated to fluorochromes and radionuclides to determine whether specific binding of peptides occurs within irradiated tumors. Immunofluorescent and immunohistochemical staining of $\beta_3$ within the lumen of blood vessels immediately following irradiation has been observed. Drug delivery to irradiated tumors in accordance with the present invention has been studied through the analysis of ligands to $\beta_3$ (vitronectin, vWF, fibronectin and fibrinogen). $^{131}$I was conjugated to these ligands to determine the biodistribution in tumor bearing mice. These studies demonstrated that 131I-fibrinogen binds specifically to tumors following exposure to ionizing radiation.

Immunoconjugates directed to radiation-induced antigens in accordance with the present invention circumvent the limitation associated with attempts in the prior art to prepare immunoconjugate delivery vehicles in that prior art immunoconjugates are limited to certain tumor types. In contrast, because antigens that are induced in irradiated vessels in all tumor types have been selected for use in the methods and compositions of the present invention, all tumor types can be targeted. This is possible because it has been observed in that the endothelium and blood components respond to oxidative stress in a similar, if not identical manner in all tumors.

Examples 7–12 provide data that demonstrates improved bioavailability and biodistribution of therapeutic agents to irradiated tissues in animal models. The methods and compositions of the present invention thus provide for an increase in the bioavailability of therapeutic agents at biologically active sites, and for a reduction in toxicity by directing treatment specifically to the neoplasm or the site of angiogenesis. Thus, an aspect of the present invention is to target drug delivery to these radiation-induced molecules through antibody conjugate delivery vehicles, protein conjugate delivery vehicles and peptide conjugate delivery vehicles.

Site-specific drug delivery to radiation-induced antigens is adaptable to many compounds and therapeutic approaches. In this regard, any suitable therapeutic agents, including but not limited to cytotoxins, biologicals, gene therapy and radionuclides can be incorporated into a delivery vehicle of the present invention.

Materials and Methods Employed in Examples 7–12

Linking Compounds. Linking compounds include 1,3,4,6-tetrachloro-3a,6a-diphenylgicouril (a reagent sold under the registered trademark IODO-GEN™), and MPBA, each available from Pierce Chemical Company, Rockford, Ill. The IODO-GEN® reagent reacts with tyrosine residues, while MPBA reacts with cysteine residues, both of which are not on the peptide HHLGGAKQAGDV (SEQ ID NO:1). An advantage of the IODO-GEN® reagent is that it is supplied in coated tubes and beads to eliminate contamination of the injectable material, whereas MPBA is in powder form. Initial experiments use the IODO-GEN® reagent to iodinate poly-tyrosine peptide on HHLGGAKQAGDV-SGSGS (SEQ ID NO:2) (HHLGGAKQAGDV-SGSGS-YYYYY (SEQ ID NO:4)), and additional experiments use MPBA to iodinate poly-Cys.

Preparation and Radioiodination of Peptides. An IODO-GEN®-plated reaction vessel (Pierce, Rockford, Ill.) is rinsed with a small amount of sterile saline to remove any loose microscopic flakes of the iodination reagent. The desired amount of carrier-free $^{125}I$ sodium iodide, a specific activity of 100 mCi/mg protein, is added to the reaction vessel, followed by the reconstituted peptides suspension. The reaction vessel is then sealed off and the reaction is allowed to proceed for 20 minutes at room temperature with constant gentle agitation of the reaction vessel. The iodination process is terminated by removing the reaction mixture from the reaction vessel into a centrifugation tube. The reaction mixture is centrifuged at 3,000 rpm for 15 minutes. The supernatant is removed and the residue is reconstituted in 5 ml sterile normal saline.

Pinhole Gamma Camera Imaging of Peptide Biodistribution. A dedicated research single-head gamma camera (20 cm×40 cm active imaging area) fitted with a cone-shaped pinhole collimator is used for nuclear medicine animal imaging experiments. The pinhole collimator, equipped with a 4 mm aperture Tungsten insert, is used to acquire pre-treatment and serial, post-treatment follow-up images of each animal in order to determine the temporal distribution of peptide in vivo. Each pinhole acquisition comprises a planar view acquired for 3 minutes using a 256×256 pixel acquisition matrix. In order to maximize pinhole collimator—gamma camera system sensitivity, a source-to-aperture distance on the order of 2 cm to 5 cm is maintained. The spatial distribution of peptide within each image is measured using quantitative, region-of-interest (ROI) analysis. Two different size ROIs are used in both the tumor region and mouse background in order to quantify image counts and isolate any possible influence of ROI size on quantification. A 2×2 (small) and 11×11 (large) pixel ROI are used to record image counts in the tumor and other organs in the mouse. The angular dependence of pinhole efficiency is measured using a flat, uniform sheet source of activity. Image counts are then corrected for decay and this geometric effect.

Statistical Considerations. Internal controls are established in each animal by use of an untreated control tumor implanted on the left hindlimb and irradiation of the right hind limb tumor, as described by Hallahan, (1995b) and by Hallahan, (1998).

Sample Size and Power Analysis. In order to calculate the statistical significance of differences between groups of mice, eight mice are studied at each time to determine statistical significance. In general, a sample size of eight per group gives about 80% of power to detect a difference of 1.5-fold S.D. in the interesting parameters between two groups with a two-sided =5%.

Statistical Analysis Plan. Pharmacokinetic parameters are presented in tabular and graphic form. Pharmacokinetic parameters such as maximal plasma concentration, time of maximal concentration, and area under the plasma concentration time curve are determined using non-compartmental methods. Statistical analyses are performed using the General Linear Model method of the Statistical Analysis System (SAS). If significant differences are indicated by the ANOVA analysis, the Waller-Duncan K-ratio t-test procedure is used for pairwise comparisons of mean pharmacokinetic parameter values.

For the single time point data, tests of hypotheses concerning correlation between imaging results and results are completed using the paired t-test or Wilcoxon Signed-Rank test for the interesting continuous parameters or the McNemar's Chi-square test for the interesting categorical parameters. For either count or binary multiple time points data, tests concerning correlation between imaging results and pharmacokinetic results are made using the Generalized Estimating Equation (GEE) method statistical procedure for longitudinal data analysis with multiple observable vectors for the same subject (Diggle, 1994; Liang, 1986). For continuous multiple time points data, tests concerning correlation between groups are completed using the restricted/residual maximum likelihood (REML)-based repeated measure model (mixed model analysis) (Jennrich, 1986) with various covariance structure.

The statistical analyses are completed by SAS 6.12 statistical program, or SAS IML macro in this project. Computer connections, when necessary, are attained via a Novell network using the Internet Packet eXchange (IPX) protocol.

Example 7

X-Ray-Guided Drug Delivery Using GP-IIb/IIIa Binding Delivery Vehicles

This Example discloses the delivery of specific activity of therapeutic radionuclides to tumors by x-ray-guided delivery of microspheres and biAPCITIDE® peptide. The objective of this Example is to improve the specificity of drug delivery to irradiated tissues by reducing nonspecific binding within the RES.

Fibrinogen is covalently bound to the surface of cross-linked human albumin in accordance with techniques disclosed in U.S. Pat. Nos. 5,069,936; 5,308,620; 5,725,804; 5,716,643; and 5,616,311, herein incorporated by reference. Briefly, fibrinogen-coated microspheres (available form Hemosphere, Inc., Irvine, Calif. as thrombspheres) ranging from 100 nm to 1 μm were produced from albumin microaggregates. The microspheres were re-suspended using 10 mL of sterile normal saline (0.9% NaCl) and 0.5 mL of the reconstituted microspheres was added to a 1.5 mL conical polypropylene tube previously coated with IODO-GEN® reagent (Pierce Chemical Company). 11.3 mCi (0.42 GBq) of I-131 in approximately 11 μL was added to the microspheres and allowed to incubate at room temperature for 30 minutes.

Following incubation, the microspheres were transferred to a 15 mL sterile centrifuge tube, diluted to 10 mL with normal saline and centrifuged at 1,500×g for 7 minutes. The supernatant was removed and discarded. The microspheres were washed one additional time with 10 mL of normal saline. Following the final wash, the microspheres were suspended in 2 mL of normal saline for injection. Final yield was 4.8 mCi (0.18 GBq) of radioiodinated microspheres in 2 mL saline. Radiochemical yield was 42.4%.

C57BL6 mice bearing Lewis Lung Carcinoma hind limb tumors were treated in three manners: 1) control mice received $^{131}$I-microspheres, but no irradiation, 2) 10 Gy prior to $^{131}$I-microspheres, 3) 10 Gy immediately after $^{131}$I-microsphere injection. Whole body gamma camera images were obtained by pinhole planer imaging. Untreated tumors showed no binding of microspheres within tumors, but there was uptake in liver and spleen. Tumors treated with 10 Gy prior to microsphere administration showed $^{131}$I uptake in tumors within 1 hour and persistent uptake in tumors beyond 24 hours. Gamma detection was also observed in the liver and spleen. Tumors treated with 10 Gy immediately after radiolabeled microsphere injection showed 10-fold greater uptake in tumors as compared to tumors treated with 10 Gy before injection. There was minimal uptake in the liver and spleen in these animals.

To provide additional observations of radiolabeled ligand binding to radiation-induced receptors, ligands that bind to receptor GPIIb/IIIa were employed. These ligands include vitronectin, fibronectin and fibrinogen (Hawiger, 1992), which can each bind to other integrin receptors. Fibrinogen was labeled with $^{131}$I using the IODO-GEN® reagent. Tumors (GI261, B16F0) were grown in the hind limb of nude and C57BL6 mice and irradiated with 4Gy as described by (Hallahan et al., 1995b; Hallahan et al., 1998a). $^{131}$I-fibrinogen was then administered by tail vein injection and gamma camera images were obtained. $^{131}$I-fibrinogen localized to tumors in all three models, suggesting that this process is not tumor-type specific. Well counts of tumors and organs verified $^{131}$I binding in tumors. Five mice were grouped into each of the experimental conditions to measure statistical significance (p<0.05). Treated and untreated tumors in mice were analyzed to show $^{131}$I-fibrinogen binding to B16F0 and GI261 tumors. Images were obtained 24 hours after sham or λ irradiation of tumors.

To observe radiolabeled ligand binding to radiation-induced receptors, ligands that bind to receptor GPIIb/IIIa were employed. These ligands include vitronectin, fibronectin and fibrinogen (Hawiger, J., and Timmons, S. (1992) *Methods in Enzymology* 215:228–233), which can each bind to other integrin receptors. Fibrinogen was labeled with $^{131}$I using iodogen. Tumors (GI261, B16F0) were grown in the hind limb of nude and C57BL6 mice and irradiated with 4Gy as described by Hallahan, D. E. et al., *Biochemical & Biophysical Research Communications* 217:784–795 (1995b) and Hallahan, D. E., et al., Cancer Research, 58:5126–5220(1998a). $^{131}$I-fibrinogen was then administered by tail vein injection and gamma camera images were obtained. $^{131}$I-fibrinogen localized to tumors in all three models, indicating that the approach is not tumor-type specific. Well counts of tumors and organs verified $^{131}$I binding in tumors. Five mice were grouped into each of the experimental conditions to measure statistical significance (p<0.05). Treated and untreated tumors in mice were analyzed to show $^{131}$I-fibrinogen binding to B16F0 and GI261 tumors. Images were obtained 24 hours after sham or λ irradiation of tumors.

To determine a preferred schedule of administration, $^{131}$I-fibrinogen was administered either immediately prior to irradiation or immediately after irradiation. $^{131}$I-fibrinogen binding was analyzed in B16F0 tumors and in GI261 tumors. Tumors were irradiated immediately after and immediately before administration of $^{131}$I-fibrinogen. A control (sham irradiation) animal was also analyzed. Tumor uptake was recorded graphically.

Site-specificity of binding to irradiated tumors was studied, and it was observed that site-specific binding of fibrinogen occurred when the $^{131}$I-fibrinogen was administered immediately after irradiation. In comparison, $^{131}$I-fibrinogen administered immediately prior to irradiation showed some non-specific binding to other organs in addition to the tumor. Fibrinogen binding to tumors requires platelet activation and subsequent GPIIb/IIIa activation. Circulating $^{131}$I-fibrinogen binds to other sites if it is not administered after irradiation. Well counts of tumors and organs verified $^{131}$I binding in tumors. Five mice were grouped into each of the experimental conditions to measure statistical significance (p<0.05). While it is not applicant's wish to be bound by a particular theory of operation, it is believed that unlabeled (cold) fibrinogen competes with $^{131}$I-fibrinogen for binding to receptors. The preferred sequence of administration is x-irradiation followed by $^{131}$I-fibrinogen administration. This sequence is used in the experiments described in Examples 7–12.

To determine the time and dose of radiation required to achieve $^{131}$I-fibrinogen binding, the time of scanning and the dosage of irradiation was varied. It was shown that $^{131}$I-fibrinogen binds within one hour of irradiation of tumors. It was also found that 2 Gy is sufficient to induce $^{131}$I-fibrinogen binding. In these experiments, time sequence of fibrinogen binding in B16F0 and GI261 tumors was observed. Images in each case were acquired at one hour post-irradiation and 24 hrs post irradiation time points.

In separate experiments, APCITIDE® peptide is labeled with $^{99}$Tc in accordance with a protocol provided by Diatide Inc, a commercial source. The APCITIDE® peptide is a fibrinogen analogue peptide that binds to GPIIb/IIIa on activated platelets, as described by Taillefer, J., *Nuc. Med.* 38:5 (1997) and by VandeSreek, P., *Eur. J. Nucl. Med.* 25:8 (1998). Radiolabeled APCITIDE® peptide is then injected by tail vein into mice bearing hind limb tumors. Mouse tumors are treated with radiation as described herein above. An optimal schedule of administration is determined.

The platelet priming agent, DDAVP (depo-provera), is contemplated to improve radiation induced platelet aggregation within tumors and thereby lower the radiation threshold dose for GP-IIb/IIIa binding. The enhancement of platelet aggregation with DDAVP is also contemplated to enhance binding of radiolabeled peptides and microspheres. Thus, in additional experiments, DDAVP is administered in conjunction with the radiolabeled peptides and microspheres and with the exposure of the target tissue to radiation. Validation of Image Processing is performed by use of autoradiography and immunofluorescence of platelets GP IIb/IIIa.

X-ray-guided drug delivery can thus be achieved by use of fibrinogen-coated microspheres and by peptides which preferentially bind activated platelets. Improved biodistribution and pharmacokinetics are observed with microspheres in that the microspheres bind more preferentially to activated platelets as compared to RES, and all activated platelets represent targets for drug delivery.

Example 8

X-Ray-Guided Drug Delivery Via Antibody Delivery Vehicles

Following platelet activation, several antigens are expressed on the surface of platelets. Indeed, it has been observed that irradiation of animal tumors increases the expression of platelet antigens such as P-selectin and GP-IIb/IIIa. As disclosed herein above, antibodies can be conjugated to radionuclides, cytotoxic agents, gene therapy vectors, liposomes and other active agents. In this Example, the administration of radioimmunoconjugate delivery vehicles against platelet antigens following irradiation of tumors is disclosed.

Anti-GP-IIb/IIIa antibodies (R&D Systems) are labeled with $^{131}$I using IODO-GEN® reagent (Pierce Chemical Company). Labeled antibody is separated from free iodine by use of column chromatography. Radioimmunoconjugates are injected into mice by tail vein. Hind limb tumors are implanted and treated as described herein above. The optimal time of administration of radioimmuno-conjugates is determined.

In separate experiments, procoagulants such as DDAVP are also administered to enhance radioimmunoconjugate binding to activated platelets in irradiated tumors. Mouse subjects are imaged by gamma camera as described herein above. Phosphoimager plates and histologic sections with immunohistochemistry as described herein above are used to validate image processing. In the event that certain radioimmunoconjugates do not achieve specific activity within tumors that is sufficient to image or treat tumors, multiple radionuclides are incorporated into the antibody delivery vehicles.

In additional experiments, Fab' fragments of anti-GPIIIa and anti-GP-IIb antibodies are also employed in binding in a site-specific manner to irradiated tumors. It is shown herein that anti-GPIIIa antibody staining in blood vessels following x-irradiation. There are two approaches in producing antibodies for site-specific binding. The first is cleavage of the IgG antibody to form the Fab' fragment. The second approach is the use of phage antibodies to GPIIIa and GP-IIb that are produced in the Vanderbilt Cancer Center Molecular Discovery Core Laboratory using phage-display techniques. Each of these approaches yields low molecular weight antibodies that can be efficiently produced for clinical studies. Specificity of the GP-IIIa (integrin $\beta_3$) antibodies and antibody fragments are compared to the specificity of the GP-IIb antibodies and antibody fragments to establish a preferred reagent and in that GP-IIIa is also found in $\alpha_v\beta_3$.

Experimental Design: The anti-GPIIIa and anti-GP-IIb antibodies (R&D Systems) are cleaved to form the Fab' fragment. This fragment is isolated from the Fc fragment by columns. In addition, GPIIIa protein is screened with a phage library within the Vanderbilt Cancer Center Molecular Discovery Core Laboratory. Antibody from phage is grown up in the bacteria. Antibodies are then studied for binding in irradiated tumors. Antibodies are labeled with $^{131}$I using IODO-GEN® reagent as described above. The molar ratio of $^{131}$I to antibody is optimized to avoid potential reduction in the affinity of antibody binding due to $^{131}$I.

Tumors are implanted and irradiated as described herein. Radio-immunoconjugates are administered immediately after irradiation using tail vein injection. Eight mice are randomly assigned into experimental and control groups. Imaging and quantification of $^{131}$I are performed as described above. Statistical analysis is performed as described above.

Positive control groups: Radiolabeled fibrinogen is administered to irradiated tumor bearing mice and compared to radioimmunoconjugates. These mice are randomly assigned into groups during the same experiment as radioimmunoconjugates.

Negative control groups: Nonirradiated control tumors are implanted in the left hind limb of all mice. Secondly, radiolabeled anti-$\alpha_v$ and anti-human IgG antibodies are administered to tumor bearing mice following irradiation to verify that antibody binding to irradiated tumors is not a generalized phenomenon.

Example 9

X-Ray-Guided Drug Delivery Targeted to Radiation-Induced Antigens in Blood Vessels Radiation-induced targets for drug delivery systems will be most useful if they are not tumor-specific. The vascular endothelium is an essential component to nearly all neoplasms. As disclosed herein above, radiation response is similar across a wide range of tumor types. In particular, P-selectin exocytosis, von Willebrand Factor release and platelet aggregation are observed within all tumor blood vessels following irradiation. In this Example, antibody delivery vehicles for x-ray-guided drug delivery to the vascular endothelium of tumors is disclosed. Antibody delivery vehicles adhere to antigens released into the lumen and are thus obstructed from circulating beyond the confines of the tumor. In view of the targeting of vascular endothelium, this Example is also illustrative of the methods of treating angiogenesis in accordance with the present invention disclosed herein above.

Additionally, one level of radiation-induced expression of receptors and adhesion molecules is the activation of inactive receptors following irradiation of tumor blood vessels. Tumors in the hind limb of mice were treated with 2 Gy ionizing radiation followed by sectioning and immunohistochemical staining for the $\beta_3$ integrin in the tumor sections. The observed histologic pattern of staining showed that both platelets and endothelium stain with anti-$\beta_3$ antibody after irradiation, but not prior to irradiation. Thus, therapeutic doses of irradiation (2 Gy) were and are sufficient to induce the accumulation of integrin $\beta_3$ within tumor blood vessels within 1–4 hours of irradiation.

Hind limb tumors are implanted into mice and treated with radiation as described by Hallahan, D. E. et al., *Cancer Research*, 58:5126–5220 (1998). Radioimmunoconjugate delivery vehicles are prepared using anti-E-selectin and anti-P-selectin antibodies (R&D Systems), IODO-GEN® reagent (Pierce Chemical Company) and $^{131}$I. Radiolabeled antibodies are separated from free $^{131}$I by use of column chromatography. The delivery vehicles are injected via tail vein into mice with hind limb tumors following treatment with irradiation. Mice are imaged with gamma camera imaging as described herein above. Image processing is validated by use of phospho imager plates, immunofluorescence and immuno-histochemistry as described herein above.

One potential limitation of this embodiment of the present invention is that anti-E-selectin antibody binding occurs in untreated normal tissues such as the lung. The importance of validation of the tumor specificity for radioimmunoconjugate delivery vehicles is that the ideal radiation-induced antigens have substantially no constitutive expression in any tissue, but prolonged expression in tumor blood vessels. Thus, pharmacokinetics and biodistribution of the anti-E-selectin and anti-P-selectin antibody delivery vehicles are also determined.

Example 10

X-ray-guided DRUG Delivery by Use of a Twelve Amino Acid Segment of the λ Subunit of Fibrinogen This Example pertains to the use of the dodecapeptide HHLGGAKQAGDV (SEQ ID NO:1), a segment of the A subunit of fibrinogen, to achieve site-specific binding to irradiated tumors. This peptide segment of the carboxyl terminus of the fibrinogen λ chain binds to GPIIb/IIIa following platelet activation. The fibrinogen binding sequence (HHLGGAKQAGDV (SEQ ID NO:1)) is sufficient for site-specific localization to irradiated tumors.

Observations: The peptide sequence within fibrinogen that binds to the activated GPIIb/IIIa receptor is the dodecapeptide HHLGGAKQAGDV (SEQ ID NO:1). To determine whether HHLGGAKQAGDV (SEQ ID NO:1) binds in irradiated tumors, applicant utilized the peptide HHLG-GAKQAGDV (SEQ ID NO:1) linked to biotin by a serine-glycine linker (HHLGGAKQAGDV-SGSGSK (SEQ ID NO:10)-eBiotin). This peptide was synthesized in the Vanderbilt University Peptide Core Lab and biotinylated at the carboxyl terminus. The resulting HHLGGAKQAGDV-SGSGSK(SEQ ID NO:10)-(eBiotin) was administered by tail vein injection into tumor bearing mice. B16F0 tumors in the hind limb were treated with sham irradiation (control), 4 Gy irradiation followed by HHLGGAKQAGDV-SGSGSK-(eBiotin) injection, or HHLGGAKQAGDV-SGSGSK-(eBiotin) followed by tumor irradiation (4 Gy). Tumors were frozen at 4 hours and sectioned for fluorescence staining. Avidin-FITC was incubated with tumor sections and imaged by UV microscopy. Avidin-FITC stained blood vessels were observed in irradiated tumors, but not in untreated control. Moreover, it was found that HHLGGAKQAGDV (SEQ ID NO:1) administration prior to irradiation is a more efficient schedule of administration as compared to radiation before dodecapeptide administration.

Design of Iodination Experiments: Tumors are implanted and irradiated as described herein above. The synthetic dodecapeptide encompassing the sequence HHLG-GAKQAGDV (SEQ ID NO:1) on the carboxyl-terminal segment of fibrinogen λ chain binds to GPIIb/IIIa is prepared, and a peptide tail for radioiodination (SGSGS-YYYYY; SEQ ID NO:13) is added. The peptide tail is commercially available from PeptidoGenic, Livermore, Calif. A sample from each batch is sequenced in accordance with standard techniques for quality control.

HHLGGAKQAGDV-SGSGS-YYYYY (SEQ ID NO:3) is labeled with $^{131}$I using IODO-GEN® reagent as described above. When tumors are grown to 0.5 cm in diameter, the tail vein of each mouse subject is cannulated and HHLG-GAKQAGDV-SGSGS-YYYYY- $^{131}$I is injected. The injection tubing and syringe is counted after the injection to measure residual $^{131}$I. Immediately after administration of $^{131}$I-peptide, tumors are irradiated using techniques described herein and by Hallahan, D. E. et al., Cancer Research, 58:5126–5220 (1998). Mice are imaged by gamma camera imaging at 1 and 24 hours after irradiation. HHLGGAKQAGDV-SGSGS-yyYYY-$^{131}$I binding to tumors is quantified by gamma camera imaging and direct well counts from excised tumors as described above. Tissue sections of all organs are analyzed. Eight tumor-bearing mice are randomly assigned into each of the experimental and control groups. Statistical considerations are addressed as described above.

Positive control groups: Radioiodinated-fibrinogen is administered to irradiated tumor bearing mice and compared to radioiodinated-peptide. These mice are randomly assigned into groups during the same experiment as radiolabeled peptides.

Negative control groups: Nonirradiated control tumors are implanted in the left hind limb of all mice. Secondly, radiolabeled SGSGSGSSGSGSSGSGS-YYYYY (SEQ ID NO:14) are administered to tumor bearing mice following irradiation to verify that peptide binding to irradiated tumors is not a generalized phenomenon.

It is noted that the three-dimensional conformation of fibrinogen might facilitate site-specific binding to irradiated tumors. Alternatively, $^{311}$I labeling might interfere with peptide binding to GPIIb/IIIa. A longer peptide linker and fewer Tyr residues are options that are employed in each case.

Example 11

Liposome Delivery Vehicle Comprising Twelve Amino Acid Segment of the a Subunit of Fibrinogen This Example pertains to the preparation of liposomes that are conjugated to the dodecapeptide HHLG-GAKQAGDV (SEQ ID NO:1), a segment of the A subunit of fibrinogen, to achieve site-specific binding to irradiated tumors.

In initial experiments, Dil (a lipid fluorescent marker) was added to liposome-fibrinogen conjugates and injected by tail vein. As a control, liposomes without fibrinogen conjugation were injected. These produced no increase in fluorescence in irradiated tumors. Fluorescence within blood vessels of tumors treated with ionizing radiation was observed for the liposome-fibrinogen conjugates. These findings support site-directed drug delivery to the fibrinogen receptor in irradiated tumors.

Cationic liposomes can be conjugated to antibodies and peptides (Kirpotin, D., et al. (1997) Biochemistry 36(1): 66–75); however, these liposomes bind to lipophilic proteins in the serum, which reduces the circulation time. Therefore, polyethyleneglycol (PEG) is used to coat the drug delivery systems. PEG prolongs circulation time (Nam, S. et al (1999) Oncol. Res., 11, 9; Koning, G. A., et al. (1999) Biochim. Biophys. Acta 20;1420(1–2):153–167.

In this Example, HHLGGAKQAGDV (SEQ ID NO:1) is conjugated to liposomes and encapsulated by PEG. It is then determined whether both large MW therapeutic proteins and small MW cytotoxic compounds can be localized to irradiated tumors by liposomes conjugated to HHLG-GAKQAGDV (SEQ ID NO:1). The linking peptide SGSGS is placed at the C-terminus, which is linked to liposomes. Liposomes are conjugated to the SH on Cys at the C-terminus. The biodistribution of HHLGGAKQAGDV-SGSGSC (SEQ ID NO:1)-liposome is studied and the length of the linking peptide is altered as necessary. In the event that PEG will not achieve membrane fusion that is comparable to cationic liposomes, the length of the linking peptide is also altered as necessary.

Preparation of HHLGGAKQAGDV (SEQ ID NO:1)-Long Circulatory Liposomes. Two methods of conjugating liposomes to peptides are employed. The first method conjugates the liposome to the N-terminus, and thus the linking peptide is placed at the N-terminus. This method arranges the conjugate in the following configuration: liposome-SGSGS-H HLGGAKQAGDVC (SEQ ID NO:12). The second method conjugates the liposome to the C-terminus of the peptide. This method is facilitated by placing a Cys residue at the N-terminus. This method arranges the conjugate into the configuration: HHLGGAKQAGDV-SGSGSC (SEQ ID NO:11)-liposome. These two methods provide alternatives in the event that one configuration is preferred for site-specific drug delivery over the other configuration. These methods are also applicable to larger polypeptides and proteins, including fibrinogen itself.

Method 1:

Step (1) Synthesis of Maleimide-PGE-PE

The lipophilic SH reactive reagent with a long spacing arm is synthesized from maleimide-PGE 2000-NSH ester (Prochem), dioleoylphosphatidylethanolanime (DOPE, Avanti Polar Lipids, Alabaster, Ala.) and triethylamine in chloroform (1:1:1.5). Resulting maleimide-PEG 2000-DOPE is purified by flash column.

Step (2) Preparation of thiolated HHLGGAKQAGDV (SEQ ID NO:1)

Under stirring, to a solution of HHLGGAKQAGDV (SEQ ID NO:1) (2 mg/mL) in 0.01 M HEPES 0.15 NaCl buffer pH7.9, containing 10 mM EDTA and 0.08% $NaN_3$ is added 5× excess of freshly prepared Traut's reagent in the same buffer. Reaction is performed for 30 minutes at 0° C. SH-HHLGGAKQAGDV is then purified using a desalting PD-10 column.

Preparation of maleimide-containing long circulating liposomes with fluorescent labels. PGE 2000-PE, cholesterol, Dipalmitoyl phosphocholine (Avanti Polar Lipids, Alabaster, Ala.), Dil (lipid fluorescent marker), and maleimide-PEG-2000-DOPE is dissolved in chloroform and mixed at a ratio of 10:43:43:2:2 in a round bottom flask as described by Leserman, (1980). The organic solvent is removed by evaporation followed by desiccation under vacuum for 2 hr. Liposomes are prepared by hydrating the dried lipid film in PBS at a lipid concentration of 10 mM. The suspension is then sonicated 3×5 minutes until clear, forming unilamellar liposomes of 100 nM in diameter.

Conjugation of thiolated HHLGGAKQAGDV (SEQ ID NO:1) to maleimide containing liposomes. Prepared vesicles and thiolated protein is mixed in 10 mm Hepes, 0.15M NaCl and EDTA pH 6.5. The final concentrations for proteins and liposomes are 0.25 g/L and 2.5 mM, respectively. Mixture is incubated for 18 hr. at RT and vesicles is separated from unconjugated protein by gel filtration (SEPHAROSE®4B-CL, Pharmacia).

Method 2:

To conjugate the peptide to long-circulating liposomes, a peptide with a Cys residue on the C-terminal is synthesized (PeptidoGenic, Livermore, Calif.). A bifunctional PEG (MW2000) with a maleic group on one end and NHS group on the other end is used to conjugate to the aminal group of dioleyol phosphatidyl ethanolamine (DOPE). The resulting maleic-PEG-DOPE serves as a sulfhydryl-reactive lipid anchor with a peptide linker between the lipid portion and the SH-reactive group. Long-circulating liposomes are prepared by reverse phase evaportation method using a lipid mixture composed of DOPC:Cholesterol:PEG-DOPE:maleic-PEG-DOPE:Cy3-DOPE at a ratio of 45:44:5:2:2 (mole ratio). The peptide is then conjugated to the liposomes at pH 7.0 under inert gas for 24 hours at room temperature. After the conjugation, the excess of peptide is removed though a gel filtration step using sepharcyl 100 column with PBS as eluent. The percentage of conjugation of the peptide to the liposomes is estimated by the reduction of free peptide peak.

Experimental Design: HHLGGAKQAGDV (SEQ ID NO:1) is conjugated to liposomes using SH-reactive group as described above. Liposomes are labeled with gamma emitters and fluorochromes so that the pharmacokinetics and biodistribution can be measured. HHLGGAKQAGDV-SGSGSC (SEQ ID NO:11)-Liposome are then coated with PEG as described above. Tumors are implanted and irradiated as described above. HHLGGAKQAGDV (SEQ ID NO:1)-conjugated encapsulated drugs are then injected by tail vein injection.

Bidistribution is studied by use of gamma emitters and gamma camera imaging. Both large MW proteins and small MW compounds (i.e. active agents) are radio-labeled. A therapeutic protein, tumor necrosis factor is labeled with $^{131}$I by use of IODO-GEN® reagent as described above. $^{131}$I-TNF is encapsulated in liposomes-HHLGGAKQAGDV (SEQ ID NO:1) conjugates and PEG administered by tail vein as described above.

Doxorubicin is used to study the biodistribution of a small MW compound that interacts with radiation. Doxorubicin is encapsulated in fluorescent liposomes (Avanti, Alabaster, Ala.) and PEG-HHLGGAKQAGDV (SEQ ID NO:1) conjugates and administered by tail vein as described above. Methods of preparing fluorescent liposomes and conjugation of HHLGGAKQAGDV (SEQ ID NO:1) to liposomes are described above, Doxorubicin levels in serum and tumors in the Pharmacokinetic core lab at Vanderbilt University using standard techniques. Fluorescence microscopy is used to measure liposomes in tumors using fluorescence quantification techniques described by Hallahan, (1997a).

Positive control groups: HHLGGAKQAGDV-SGSGS-YYyyY-$^{131}$I is administered to one group of irradiated tumor bearing mice and compared to biodistribution of encapsulated radiolabeled liposome. These mice are randomly assigned into groups during the same experiment as radiolabeled drugs. Radiolabeled drug binding in each group is quantified and compared to the HHLGGAKQAGDV-SGSGS-YYYYY-$^{131}$I positive control group.

Negative control groups: Firstly, control tumors are implanted in the left hind limb of all mice and remain unirradiated. Secondly, SGSGSSGSGSGS-SGSGS (SEQ ID NO:14) are conjugated to PEG and liposomes and administered to tumor bearing mice following irradiation to verify that encapsulated drug binding to irradiated tumors is not a generalized phenomenon. Eight tumor-bearing mice are randomly assigned into each of the experimental and control groups. Statistical considerations are described above.

Example 12

Targeting Ad Vectors to the Vascular Endothelium by Use of X-Rays

Adenovirus (Ad) genome encodes a fiber protein that initiates binding to receptors. The fiber protein contains 3 H1 segments that are required for binding. This segment can be modified to alter Ad binding to other targets. This Example pertains to the insertion of DNA encoding the binding peptide RGD into the H1 coding region achieve site-specific Ad binding to irradiated tumor blood vessels. The replication-incompetent Adenovirus vectors AdTNF.F(RGD) and AdZ.F(RGD) achieve reporter gene expression in tumor blood vessels.

To evaluate Ad vector binding to irradiated tumor blood vessels, an RGD modified adenoviral vector Ad (AdZ.F (RGD)) was administered by tail vein ($5\times10^8$ PFU) immediately prior to irradiation. The Ad vector was modified in accordance with standard techniques to express an RGD sequence as described herein in the protein coat of the viral vector.

LacZ reporter gene expression was studied by immunofluorescence. β-galactosidase expression was studied in untreated control GL261 gliomas implanted into C57BL6 mice. The AdZ wild type vector expressing beta-galactosidase was administered by intravascular injection. Likewise, the RGD modified adenovirus, AdZ.F(RGD) was administered to irradiated tumors by intravascularadministration. Expression in tumor endothelium was determined by immunofluorescence using the anti-*E. coli* β-gal antibody, which recognizes the gene product of LacZ (β-gal) but not human or mouse β-gal. A seven-fold increase in β-gal expression was observed in irradiated tumors.

Ad vector gene delivery to tumor endothelium is optionally coupled with the fibrinogen-liposome drug delivery described above. In this case, positive and negative controls (intratumoral injection and unmodified Ad by tail vein) are also used. The biodistribution of gene therapy guided by a fibrinogen conjugate to radiation-induced proteins within the tumor vasculature is assessed. The dodecapeptide (e.g. SEQ ID NO:1) ligand to GPIIb/IIIa or alternative GP-binding peptide can also be inserted into the H1 region.

The Ad vector can further comprise a nucleic acid molecule encoding a cytotoxic gene product that has been shown to interact with radiation is needed. An Ad.TNF vector enhances the effects of radiation on tumor regression and tumor control in animal models (Hallahan, D. E., et al. (1995b) *Nature Medicine* 1:786–791). Expression of the tumor necrosis factor gene (TNF) is under the regulation of the radiation-inducible promoter Egr-1. Tumors treated with Ad.TNF and radiation undergo vascular obliteration and subsequent necrosis (Hallahan, 1995b). Thus, intravascular administration of AdTNF.F(RGD) will achieve TNF expression in tumor vessels leading to necrosis and tumor regression.

REFERENCES

The references listed below as well as all references cited in the specification are incorporated herein by reference to the extent that they supplement, explain, provide a background for or teach methodology, techniques and/or compositions employed herein.

Ausprunk et al., Am. J. Pathol., 79:597–618 (1975).
Ausubel et al., Current Protocols in Molecular Biology, Greene Publishing Associates and Wiley Interscience, N.Y. (1989).
Bacq, Z. M. et al., Journal of Physiology 273:42P–43P (1977).
Barkalow, F. J., et al., Blood 88:4585 (1996).
Baxter, L. and Jain, R., Microvascular Research 37: 77–104, 1989.
Becerril, B., et al., Biochem. Biophys. Res. Comm. 255: 386–393 (1999)
Bittner et al., Methods in Enzymol. 153:516–544 (1987).
Boukerche, H., British Journal of Haematology 92:442–51 (1996).
Brooks, P. C., Cancer Metastasis Rev 15:187–194 (1996).
Carrell, N., et al. (1985) J. Biol. Chem. 260:1743.
Chang, M., et al. (1999) Blood 93:2515–24.
Chen, C. S. and Hawiger, J. (1991) Blood 77: 2200–6.
Cheresh, D., (1987) Proc. Natl. Acad. Sci. USA 84:6471–6475.
Colberre-Garapin et al., J. Mol. Biol. 150:1 (1981).
Crawford, N., Semin. Intervent. Cardiol. 1:91–102 (1996).
D. Cheresh, et al., Cell 79:1157 (1997)
DeAnglis, A. et al., (1995) J Pharm Sciences, 84:39–403.
Desai, S. & Libutti, S. (1999) J Immunother, 22(3):186–211.
DeVita, V. T. Jr., in Harrison's Principles of Internal Medicine, p. 68, McGraw Hill Book Co., N.Y. (1983).
Diggle, P., et al., Analysis of longitudinal data (1994) Oxford: Clarendon Press.
Dillman et al,. Antibody Immunocon. Radiopharm 1:65–77 (1988). European Patent No. 44167
Eyden, B. P., Journal of Submicroscopic Cytology & Pathology 25:145–8 (1993).
Fletcher, G. H., Textbook of Radiotherapy. Philadelphia, Lea and Febiger (1975).
Flickinger & Trost, Eu. J. Cancer 12(2):159–60 (1976).
Folkman, J., N Engi J Med 28;333(26):1757–1763 (1995).
Frangos J. A., et al. Science, 227: 1477–79, (1985)
Gabe, D. Radiotherapy & Oncology 30:199–205 (1994).
Ghose et al., Meth. Enzymology 93:280–333 (1983).
Ghose et al., CRC Critical Reviews in Therapeutic Drug Carrier Systems 3:262–359 (1987).
Giannessi, D. et al., Nucl. Med. Biol. 22(3):399–403 (1996).
Griffiths, G. L., et al. (1994b) Nuclear Medical Biology, 2, 649–655.
Griffiths, G. L., et al., (1994a). Cancer, 73, Supplement.
Hailing et al., Nuci Acids Res 13:8019–8033 (1985).
Hainfeld, J. Proc. Natl. Acad. Sci. USA 89:11064–11068 (1992)
Hallahan et al., Cancer Research, 58:5126–5220 (1998a).
Hallahan, D. E. and Virudachalam, S., Proc. Natl. Acad. Sci. USA 94:6432–7 (1997).
Hallahan, D. E. et al., Cancer Research 56:5150–5155 (1996b).
Hallahan, D. E. et al., Biochemical & Biophysical Research Communications 217:784–795 (1995b).
Hallahan, D. E. et al., Nature Medicine 1:786–791 (1995).
Hallahan, D. E. and Virudachalam, S., Cancer Research 57:2096–2099 (1997b).
Hallahan, D. E. (1996a) Seminars in Radiation Oncology. 6:250–267
Hallahan, D. E., et al. (1997a). Radiation Research, 147, 4147.
Hallahan, D. E., et al. (1998b). Cancer Research, 58, 5484–8.
Hallahan, D. E. & Virudachalam, S. (1999a). Radiation Research 152:6–13.

Hallahan, D., et al. (1999b). Oncology 13.
Hallahan, D. E., et al. (1999c). Gene Therapy In Press.
Hallahan, D. E. and Sierra-Rivera, E (1999d) International J. Radiat. Oncol. Biol. Phys., ASTRO Supplement.
Hawiger, J., In: Molecular Cardiovascular Medicine, Sci. Am., (1995).
Hawiger, J. et al. (1982) Proc. Natl. Acad. Sci. USA 79:2068.
Hawiger, J. et al. (1989) Biochemistry 28:2909.
Hawiger, J., and Timmons, S. (1992) Methods in Enzymology 215:228–233.
Hsu-Lin, C. L. et al. Journal of Biological Chemistry 259: 9121–6 (1984)
Huwyler, J., et al. (1996) Proc. Natl. Acad. Sci. USA 26;93(24):14164–9
Inouye et al., Nucleic Acids Res. 13:3101–3109 (1995).
Ito, T., et al. (1991) Cancer Res. 51:255–260.
Johnston, R. G., et al. (1989) Cell 56:1033–44
Jennrich, R. and Schluchter, M. D. (1986) Biometrics 42:805–820.
Kantak, S. S., et al. (1993) International Journal of Radiation Biology 64:319–28.
Kasahara, N., et al. (1994) Science 266:1373–6.
Kimura et al., Immunogenetics 11:373–381 (1980).
Kirpotin, D., et al. (1997) Biochemistry (1997 Jan. 7) 36(1):66–75
Knowles and Thorpe, Anal. Biochem. 120:440–443 (1987).
Kohler and Milstein, Nature 256:495–497 (1975).
Kong, H. and Crystal, R. G., Journal of the National Cancer Institute 90:273–286 (1998).
Koning G. A., et al (1999) Biochim Biophys Acta 20:1420 (1–2):153–167
Kwok, C. S. et al. (1985) Med. Phys. 12:405.
Lamb et al., Eur Jrnl Biochem 148:265–270 (1985).
Leserman, L. D. et. al (1980) "Techniques of lipidology" pp. 113–115 Nature 299:602–604
Liang, K., Zeger, SL. (1986) Biometrika 73:13–22.
Lin, P., et al., Proc. Natl. Acad. Sci. USA 95(15): 8829–8834 (1998).
Logan et al., Proc. Natl. Acad. Sci. USA 81:3655–3659 (1984).
Lord et al., In Genetically Engineered Active Agents (Ed. A. Frank, M. Dekker Publ., p. 183) (1992).
Lowy et al., Cell 22:817 (1980).
Malik, A. & Lo, S. (1996) Pharmacological Reviews 48(2): 213–29.
Mauceri, H., et al. (1996b). Cancer Research, 56:4311–4314.
Nam, S., et al (1999) Oncol. Res. 11:9.
Peters, M., et al. (1999) Exp. Lung Res. 25(3):183–97.
Markoe, A. M., Radiation Oncologic Emergencies, in Principles and Practice of Radiation Oncology 1267–1270 (1987).
Mayadas et al. Cell 74:541–54 (1993).
Miyagami, M. and Nakamura, S., Noshuyo Byori 13:107 (1996).
Mulligan et al., Proc. Natl. Acad. Sci. USA 78:2072 (1981).
O'Hare et al., Proc. Natl. Acad. Sci. USA 78:1527 (1981).
O'Hare et al., FEBS Lett 210:731 (1987).
Ogata et al., J. Biol. Chem. 256:20678–20685 (1990).
Oriuchi, N. et al., European Journal of Nuclear Medicine 25(3):247–252 (1998).
Ossonski et al., Cancer Res., 40:2300–2309 (1980).
Pietersz et al., Antibody Immunocon. Radiopharm. 1:79–103 (1988).
Remington's Pharmaceutical Sciences, 16th Ed. Mack Publishing Company (1980).
Robertson, J. S. et al., Radiology 140(1):169–176 (1981).
Ruther et al., EMBO J. 2:1791 (1983).
Sambrook et al., Molecular Cloning, A Laboratory Manual, Cold Spring Harbor Laboratory, N.Y. (1989).
Santerre et al., Gene 30:147 (1984).
Scott-Burden, T., et al. Circulation 98:11339–45 (1998).
Sinha, S. and Wagner, D. D. (1987) European Journal of Cell Biology 43:377–83.
Sirois, E., et al. Biomaterials 19:1925–34, (November 1998).
Seung, L., et al. (1995). Cancer Research 55:5561–5.
Smith et al, J. Virol. 46:584 (1985).
Spitler L. E., et al. Cancer Res. 47:1717 (1987).
Staba, M., et al. (1999) Cancer Gene Therapy 7(2).
Staba, M. J., et al. (1998) Gene Therapy 5:293–300.
Subramaniam et al., Blood 87:123842 (1996).
Suga, K. et al., Clin Nucl Med 8:595–601 (1996).
Szybalska et al., Proc. Natl. Acad. Sci. USA 48:2026 (1962).
Taillefer, J., Nucl. Med. 38:5 (1997).
Tangemann, K., et al. (1998) J. Immunol. 161:6330.
Thorpe et al., Cancer Res. 47:5924–5931 (1987).
Tseng, Y. L., et al. (1999) Int. J. Cancer 1;80(5):723–30.
U.S. Pat. No. 4,215,051
U.S. Pat. No. 4,340,535
U.S. Pat. No. 4,472,509
U.S. Pat. No. 5,069,936
U.S. Pat. No. 5,292,524
U.S. Pat. No. 5,308,620
U.S. Pat. No. 5,328,840
U.S. Pat. No. 5,612,318
U.S. Pat. No. 5,616,311
U.S. Pat. No. 5,641,755
U.S. Pat. No. 5,716,643
U.S. Pat. No. 5,725,804
U.S. Pat. No. 5,753,230
U.S. Pat. No. 5,770,581
U.S. Pat. No. 5,776,427
U.S. Pat. No. 5,817,636
U.S. Pat. No. 5,969,936
U.S. Pat. No. 6,043,094
U.S. Pat. No. 6,045,821
U.S. Pat. No. 6,045,822
U.S. Pat. No. 6,048,546
Vaickus et al., Cancer Invest. 9:195–209 (1991).
Van Heeke et al., 264:5503–5509 (1989).
VandeSreek, P., Eur. J. Nucl. Med. 25:8 (1998).
Vogel & Muller-Eberhard, Anal. Biochem 118(2):262–268 (1981).
Wessels, B. W. and Rogus, R. D. Med. Phys. 11:638 (1984).
Wigler et al., Cell 11:223 (1977).
Wigler et al., Proc. Natl. Acad. Sci. USA 77:3567 (1980).
Wu et al., British Journal of Cancer 68:883–9 (1994).
Zola, Monoclonal Antibodies: a Manual of Techniques, CRC Press, Inc. (1987).

It will be understood that various details of the invention can be changed without departing from the scope of the invention. Furthermore, the foregoing description is for the purpose of illustration only, and not for the purpose of limitation—the invention being defined by the claims.

What is claimed is:

1. A delivery vehicle for use in targeted delivery of an active agent, the delivery vehicle comprising:
   (i) a targeting agent that preferentially binds a radiation inducible target selected from the group consisting of ICAM-1, P-selectin, β₃ Integrin, an activated platelet, and combinations thereof in a target tissue;
   (ii) a pharmaceutically acceptable diluent or excipient; and
   (iii) an active agent comprising a toxin, a radiosensitizing agent, or combinations thereof.

2. The delivery vehicle of claim 1, wherein the targeting agent is selected from the group consisting of a protein; a peptide; an antibody; a genetic construct; and combinations thereof.

3. The delivery vehicle of claim 1, comprises fibrinogen or a peptide fragment or analog thereof.

4. The delivery vehicle of claim 3, wherein the peptide fragment of fibrinogen is a gamma subunit peptide fragment of fibrinogen.

5. The delivery vehicle of claim 4, wherein the gamma subunit peptide fragment of fibrinogen comprises any of SEQ ID NOs:1–10, or comprises an analog or fragment of any of SEQ ID NOs:1–10.

6. A delivery vehicle for use in targeted delivery of an active agent, the delivery vehicle comprising a targeting agent and a pharmaceutically acceptable diluent or excipient, wherein the targeting agent comprises a gamma subunit peptide fragment of fibrinogen and preferentially binds a radiation inducible target in a target tissue, wherein the gamma subunit peptide fragment of fibrinogen comprises HHLGGAKQAGDV (SEQ ID NO:1).

7. The delivery vehicle of claim 1, wherein the delivery vehicle further comprises an imaging agent.

8. The delivery vehicle of claim 7, wherein the imaging agent is selected from the group consisting of a paramagnetic imaging agent, a radioactive imaging agent, and a fluorogenic imaging agent.

9. The delivery vehicle of claim 8, wherein the radioactive imaging agent is selected from the group consisting of gamma-emitters, positron-emitters and x-ray-emitters.

10. The delivery vehicle of claim 7, wherein the radioactive imaging agent is selected from the group consisting of $^{43}$K, $^{52}$Fe, $^{57}$Co, $^{67}$Cu, $^{68}$Ga, $^{77}$Ga, $^{81}$Br, Rb/$^{81M}$Kr, $^{87M}$Sr, $^{99M}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb and $^{206}$Bi.

11. The delivery vehicle of claim 7, wherein the radioactive imaging agent is present in the delivery vehicle in an amount ranging from about 0.1 to about 100 millicuries.

12. The delivery vehicle of claim 11, wherein the radioactive imaging agent is present in the delivery vehicle in an amount ranging from about 1 to about 10 millicuries.

13. The delivery vehicle of claim 12, wherein the radioactive imaging agent is present in the delivery vehicle in an amount ranging from about 2 to about 5 millicuries.

14. The delivery vehicle of claim 13, wherein the radioactive imaging agent is present in the delivery vehicle in an amount ranging from about 1 to about 5 millicuries.

15. The delivery vehicle of claim 1, wherein the delivery vehicle further comprises a therapeutic agent is selected from the group consisting of a chemotherapeutic agent, a radiotherapeutic agent, a and combinations thereof.

16. The delivery vehicle of claim 15, wherein the chemotherapeutic agent is selected from the group consisting of an anti-tumor drug, a cytokine, an anti-metabolite, an alkylating agent, a hormone, methotrexate, doxorubicin, daunorubicin, cytosine arabinoside, etoposide, 5–4 fluorouracil, melphalan, chlorambucil, a nitrogen mustard, cyclophosphamide, cis-platinum, vindesine, vinca alkaloids, mitomycin, bleomycin, purothionin, macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin, and combinations thereof.

17. The delivery vehicle of claim 1, wherein the toxin is selected from the group consisting of Russell's Viper Venom, activated Factor IX, activated Factor X, thrombin, phospholipase C, cobra venom factor, ricin, ricin A chain, *Pseudomonas* exotoxin, diphtheria toxin, bovine pancreatic ribonuclease, pokeweed antiviral protein, abrin, abrin A chain, gelonin, saporin, modeccin, viscumin, volkensin and combinations thereof.

18. The delivery vehicle of claim 15, wherein the radiotherapeutic agent is selected from the group consisting of $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$Bi, $^{32}$P, $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, and $^{197}$Hg.

19. The delivery vehicle of claim 1, wherein the radiosensitizing agent is selected from the group consisting of an anti-angiogenic agent; a DNA protein kinase inhibitor; a tyrosine kinase inhibitor; a DNA repair enzyme inhibitor; nitroimidazole; metronidazole; misonidazole; a genetic construct comprising an enhancer-promoter region which is responsive to radiation, and at least one structural gene whose expression is controlled by the enhancer-promoter; boron-neutron capture reagents; and combinations thereof.

20. The delivery vehicle of claim 19, wherein the genetic construct comprises a viral vector.

21. The delivery vehicle of claim 15, wherein the therapeutic agent is a chemotherapeutic agent, and the delivery vehicle comprising the chemotherapeutic agent is administered in an amount ranging from about 10 to about 1000 mg.

22. The delivery vehicle of claim 21, wherein the delivery vehicle comprising the chemotherapeutic agent is administered in an amount ranging from about 50 to about 500 mg.

23. The delivery vehicle of claim 22, wherein the delivery vehicle comprising the chemotherapeutic agent is administered in an amount ranging from about 100 to about 250 mg.

24. The delivery vehicle of claim 1, wherein the active agent is a toxin, and the delivery vehicle comprising the toxin is administered in an amount ranging from about 1 to about 500 μg.

25. The delivery vehicle of claim 24, wherein the delivery vehicle comprising the toxin is administered in an amount ranging from about 10 to about 100 μg.

26. The delivery vehicle of claim 25, wherein the delivery vehicle comprising the toxin is administered in an amount ranging from about 20 to 50 μg.

27. The delivery vehicle of claim 15, wherein the therapeutic agent is a radiotherapeutic agent, and the delivery vehicle comprising the radiotherapeutic agent is administered in an amount ranging from about 0.5 to about 100 mg.

28. The delivery vehicle of claim 27, wherein the delivery vehicle comprising the radiotherapeutic agent is administered in an amount ranging from about 1 to about 50 mg.

29. The delivery vehicle of claim 28, wherein the delivery vehicle comprising the radiotherapeutic agent is administered In an amount ranging from about 5 to about 10 mg.

30. The delivery vehicle of claim 1, further comprising a carrier.

31. The delivery vehicle of claim 30, wherein the carrier and the targeting agent are the same.

32. The delivery vehicle of claim 30, wherein the carrier is selected from the group consisting of a platelet; a leukocyte; a protein; a peptide; an antibody; a microsphere; a liposome; a genetic construct; and combinations thereof.

33. A The delivery vehicle of claim 32, wherein the carrier comprises
a liposome.

34. The delivery vehicle of claim 33, wherein the liposome comprises a lipid selected from the group consisting of phosphatidylcholines (lecithins) (PC), phosphatidylethanolamines (PE), lysolecithins, lysophosphatidylethanolamines, phosphatidylserines (PS), phosphatidylglycerols (PG), phosphatidylinositol (PI), sphingomyelins, cardiolipin, phosphatidic acids (PA), fatty acids, gangliosides, glucolipids, glycolipids, mono-, di or triglycerides, ceramides, cerebrosides and combinations thereof.

35. The delivery vehicle of claim 34, wherein the liposome comprises a cationic lipid selected from the group consisting of 1,2-dioleyloxy-3-(trimethylamino) propane (DOTAP); N-[1-(2,3, -ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy) propyl]-N,N,N-trimethylammonium chloride (DOTMA); 3β[N-(N',N'-dimethylaminoethane)carbamoly] cholesterol (DC-Choi); and dimethyldioctadecylammonium (DDAB); dioleoylphosphatidyl ethanolamine (DOPE), cholesterol-containing DOPC, and combinations thereof.

36. The delivery vehicle of claim 33, wherein the liposome comprises a hydrophilic polymer coating and the hydrophilic polymer is selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and combinations thereof.

37. The delivery vehicle of claim 33, wherein the targeting agent preferentially binds an activated platelet.

38. The delivery vehicle of claim 33, wherein the targeting agent is selected from the group consisting of a protein; a peptide; an antibody; a genetic construct; and combinations thereof.

39. The delivery vehicle of claim 33 wherein the targeting agent is fibrinogen or a peptide fragment or analog thereof.

40. The delivery vehicle of claim 39, wherein the peptide fragment of fibrinogen is a gamma subunit peptide fragment of fibrinogen.

41. The delivery vehicle of claim 40, wherein the gamma subunit peptide fragment of fibrinogen comprises any of SEQ ID NOs:1–10, or comprises an analog or fragment of any of SEQ ID NOs:1–10.

42. A delivery vehicle for use in targeted delivery of an active agent, the delivery vehicle comprising a targeting agent and a pharmaceutically acceptable diluent or excipient, wherein the targeting agent preferentially binds a radiation inducible target selected from the group consisting of ICAM-1, P-selectin, $\beta_3$ integrin, and combinations thereof, wherein the targeting agent is a gamma subunit peptide fragment of fibrinogen that comprises HHLGGAKQAGDV (SEQ ID NO:1).

43. The delivery vehicle of claim 1, wherein the radiation inducible target is a cell adhesion molecule.

44. The delivery vehicle of 2, wherein the targeting agent is an antibody or derivative thereof.

45. The delivery vehicle of claim 44, wherein the antibody or derivative thereof preferentially binds a radiation inducible target selected from the group consisting of ICAM-1, P-selectin, $\beta_3$ integrin, and combinations thereof.

46. A delivery vehicle for use in targeted delivery of an active agent, the delivery vehicle comprising:

(a) a liposome carrier:

(b) a targeting agent that preferentially binds a radiation inducible target; and (c) a pharmaceutically acceptable diluent or excipient, wherein the targeting agent is an antibody or derivative thereof selected from the group consisting of an intact immunoglobulin molecule, a single chain immunoglobulin molecule, an Fab fragment, an Fab' fragment, an F(ab')$_2$ fragment, an F(v) fragment, a single-chain Fv antibody (scFv), a humanized antibody, and a monoclonal antibody.

47. A delivery vehicle, for use in targeted delivery of an active agent, the delivery vehicle comprising a targeting agent and a pharmaceutically acceptable diluent or excipient, wherein the targeting agent preferentially binds a radiation inducible target selected from the group consisting of ICAM-1, P-selectin, $\beta_3$ integrin, and combinations thereof wherein the active agent comprises a genetic construct comprising a viral vector, an enhancer promoter region which is responsive to radiation, and at least one structural gene whose expression is controlled by the enhancer promoter.

* * * * *

SEQUENCE LISTING

<160> NUMBER OF SEQ ID NOS: 14

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit

<400> SEQUENCE: 1

His His Leu Gly Gly Ala Lys Gln Ala Gly Asp Val
  1               5                  10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit with
      linker peptide sequence

<400> SEQUENCE: 2

His His Leu Gly Gly Ala Lys Gln Ala Gly Asp Val Ser Gly Ser Gly
  1               5                  10                  15

Ser

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit with
      linker peptide and tail

<400> SEQUENCE: 3

His His Leu Gly Gly Ala Lys Gln Ala Gly Asp Val Ser Gly Ser Gly
  1               5                  10                  15

Ser Tyr Tyr Tyr Tyr Tyr
            20

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit

<400> SEQUENCE: 4

His His Ile Gly Gly Ala Lys Gln Ala Gly Asp Val
  1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit

<400> SEQUENCE: 5

His His Leu Gly Gly Ala Arg Gln Ala Gly Asp Val

-continued

```
<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit

<400> SEQUENCE: 6

His His Leu Gly Gly Ala Lys Gln Ala Gly Asp Ala
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit

<400> SEQUENCE: 7

His His Ile Gly Gly Ala Lys Gln Ala Gly Asp Ala
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit

<400> SEQUENCE: 8

His His Ile Gly Gly Ala Arg Gln Ala Gly Asp Ala
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit

<400> SEQUENCE: 9

His His Leu Gly Gly Ala Lys Gln Ala Gly Glu Val
 1               5                  10

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit

<400> SEQUENCE: 10

His His Leu Gly Gly Ala Lys Gln Ala Gly Asp Val Ser Gly Ser Gly
 1               5                  10                  15

Ser Lys

<210> SEQ ID NO 11
<211> LENGTH: 18
<212> TYPE: PRT
<213> ORGANISM: Artificial Sequence
```

```
<220> FEATURE:
<223> OTHER INFORMATION: Description of Artificial Sequence: Synthesized
      Fragment of Human Fibrinogen Gamma Subunit

<400> SEQUENCE: 11

His His Leu Gly Gly Ala Lys Gln Ala Gly Asp Val Ser Gly Ser Gly
 1               5                  10                  15

Ser Cys

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthesized
      Fragment of Human Fibrinogen Gamma Subunit

<400> SEQUENCE: 12

Ser Gly Ser Gly Ser His His Leu Gly Gly Ala Lys Gln Ala Gly Asp
 1               5                  10                  15

Val Cys

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthesized
      Linker Peptide

<400> SEQUENCE: 13

Ser Gly Ser Gly Ser Tyr Tyr Tyr Tyr Tyr
 1               5                  10

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthesized
      Glycine Serine Peptide

<400> SEQUENCE: 14

Ser Gly Ser Gly Ser Ser Gly Ser Gly Ser Gly Ser Ser Gly Ser Gly
 1               5                  10                  15

Ser
```